(12) United States Patent
Deol et al.

(10) Patent No.: US 8,932,851 B2
(45) Date of Patent: Jan. 13, 2015

(54) **METHOD AND CULTURE MEDIUM FOR ENHANCED DETECTION OF *MYCOBACTERIUM***

(71) Applicants: Parampal Deol, Raleigh, NC (US);
Leticia Barton, Raleigh, NC (US);
Yoany Portilla, Chapel Hill, NC (US);
Douglas Lovern, Durham, NC (US)

(72) Inventors: Parampal Deol, Raleigh, NC (US);
Leticia Barton, Raleigh, NC (US);
Yoany Portilla, Chapel Hill, NC (US);
Douglas Lovern, Durham, NC (US)

(73) Assignee: bioMérieux, Inc., Durham, NC (US)

( * ) Notice: Subject to any disclaimer, the term of this patent is extended or adjusted under 35 U.S.C. 154(b) by 0 days.

(21) Appl. No.: 13/741,972

(22) Filed: Jan. 15, 2013

(65) Prior Publication Data
US 2014/0199724 A1 Jul. 17, 2014

Related U.S. Application Data

(62) Division of application No. 12/827,387, filed on Jun. 30, 2010, now Pat. No. 8,389,268.

(60) Provisional application No. 61/269,977, filed on Jul. 1, 2009.

(51) Int. Cl.
*C12M 1/34* (2006.01)
*C12M 3/00* (2006.01)
*C12M 1/00* (2006.01)
*C12N 1/12* (2006.01)
*C12N 1/20* (2006.01)
*C12Q 1/04* (2006.01)

(52) U.S. Cl.
CPC .................................. *C12Q 1/04* (2013.01)
USPC ................. 435/288.1; 435/283.1; 435/253.1; 435/253.6; 435/34

(58) Field of Classification Search
CPC combination set(s) only.
See application file for complete search history.

(56) References Cited

U.S. PATENT DOCUMENTS

| | | | |
|---|---|---|---|
| 3,935,073 A | | 1/1976 | Waters |
| 3,983,003 A | * | 9/1976 | Skinsnes et al. ............... 435/244 |
| 4,666,850 A | | 5/1987 | Mehl et al. |
| 4,769,332 A | * | 9/1988 | Siddiqi et al. ................. 435/244 |
| 5,494,796 A | | 2/1996 | Spears et al. |
| 6,168,930 B1 | | 1/2001 | Horn |
| 6,579,694 B2 | | 6/2003 | Heifets et al. |
| 6,617,161 B2 | | 9/2003 | Luyten et al. |
| 6,664,096 B2 | | 12/2003 | Zhang |
| 6,951,733 B2 | | 10/2005 | Heifets et al. |
| 7,101,701 B2 | | 9/2006 | Whitlock |
| 2001/0055787 A1 | | 12/2001 | Heifets et al. |
| 2005/0079570 A1 | | 4/2005 | Kocagoz |
| 2005/0202518 A1 | * | 9/2005 | Vedrine et al. ............... 435/7.32 |

FOREIGN PATENT DOCUMENTS

| | | |
|---|---|---|
| EP | 0076647 | 4/1983 |
| EP | 0489392 A2 | 6/1992 |
| WO | 00/52139 | 9/2000 |
| WO | WO 00/52139 A1 * | 9/2000 |
| WO | 2007/136781 | 11/2007 |

OTHER PUBLICATIONS

Lynn et al. Applied and Environmental Microbiology, Nov. 1979, p. 806-810.*
Carricajo, A. et al. Evaluation of BacT/ALERT 3D liquid culture system for recovery of Mycobacteria from clinical specimens using sodium dodecyl (lauryl) sulfate—NaOH decontamination, J. Clin. Micro. 39(10):3799-3800 (Oct. 2001).
Tian, et al. Variant tricarboxylic acid cycle in *Mycobacterium tuberculosis:* Identification of alpha-ketoglutarate decarboxylase, PNAS 102(3):10670-10675 (Jul. 2005).
Singh, et al. Kinetic modeling of tricarboxylic acid cycle and glyoxylate bypass in *Mycobacterium tuberculosis,* and its application to assessment of drug targets, Theoretical Biology and Medical Modeling 3(27) (2006).
Mirrett, et al. Controlled clinical comparison of VersaTREK and BacT/ALERT blood culture systems, J. Clin. Micro. 45 (2):299-302 (Feb. 2007).
Mirrett, et al. Comparison of the VersaTREK and the BacT/ALERT blood culture systems for the growth of fastidious microorganisms, American Society of Microbiology, Poster C-214, Orlando, FL (2005) (Poster).
Mirrett, et al. Comparison of the VersaTREK and the BacT/ALERT blood culture systems for the growth of fastidious microorganisms, American Society of Microbiology, Poster C-214, Orlando, FL (2005) (Paper).
Nakamura Multiplication of *Mycobacterium lepraemurium* in cell-free medium containing ketoglutaric acid and cytochrome c, J. Gen. Microbiol., 73(1):193-195 (Nov. 1972).
Palomino, et al. Tuberculosis textbook, Chapter 14: New diagnostic methods pp. 441-486 (Jan. 2007).
Gallagher, J. et al. A selective oleic acid albumin agar medium for the cultivation of *Mycobacterium bovis,* J. Hygiene, 79(1):155-160 (Aug. 1977).
Lynn, M. et al. Role of bovine serum albumin in the nutrition of *Mycobacterium tuberculosis,* App. Env. Microbiol., 38 (5):806-810 (Nov. 1979).

(Continued)

*Primary Examiner* — Chris R Tate
*Assistant Examiner* — Douglas F White

(57) ABSTRACT

The present invention relates to an improved culture medium and method for the enhanced growth and detection of *Mycobacterium* growth. The invention further relates to an improved mycobacterial reagent system or kit that can be used for the enhanced growth and detection of *Mycobacterium.*

10 Claims, 10 Drawing Sheets

(56) References Cited

OTHER PUBLICATIONS

De Smet, K. et al. Alterations of a single amino acid residue reverses fosfomycin resistance of recombinant MurA from *Mycobacterium tuberculosis,* Microbiology, 145:3177-3184 (Nov. 1999).
BacT/ALERT MP Package Insert, Jul. 2008.
BacT/ALERT MB Package Insert, Jul. 2008.
The International Search Report for PCT/US2010/040564 dtd Dec. 20, 2010.
The International Search Report for PCT/US2010/040559 dtd Oct. 21, 2010.
Co-pending U.S. Appl. No. 12/827,338 "Method and Culture Medium for Enhanced Detection of *Mycobacterium*" Jun. 30, 2011.

* cited by examiner

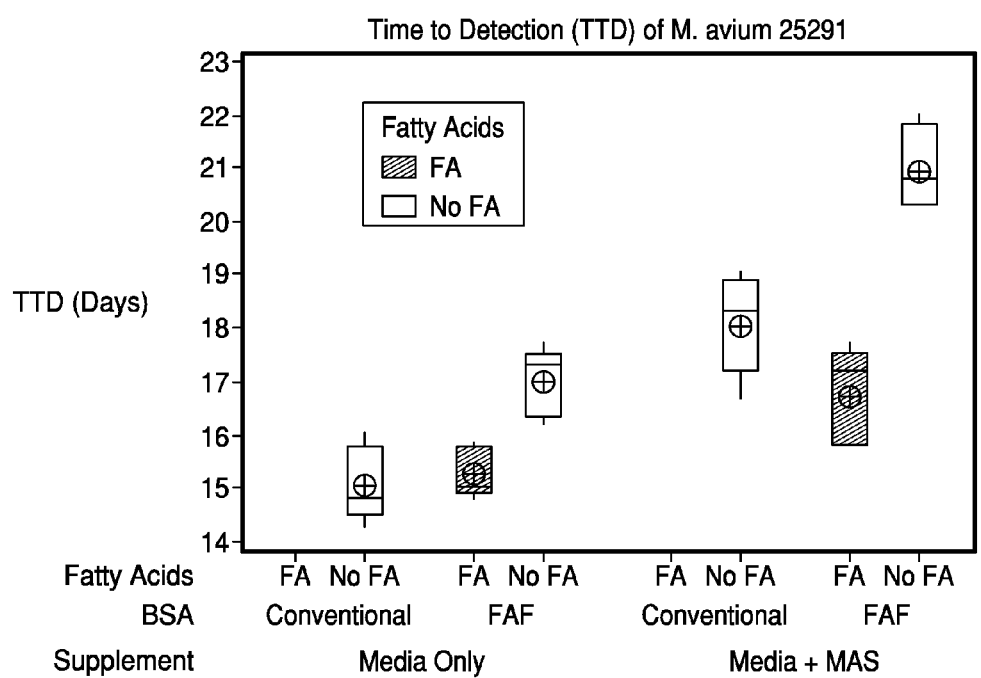

Fig. 5C

Time to Detection (TTD) of M. avium 569

Fig. 5D

Time to Detection (TTD) of M. intracellulare 13950

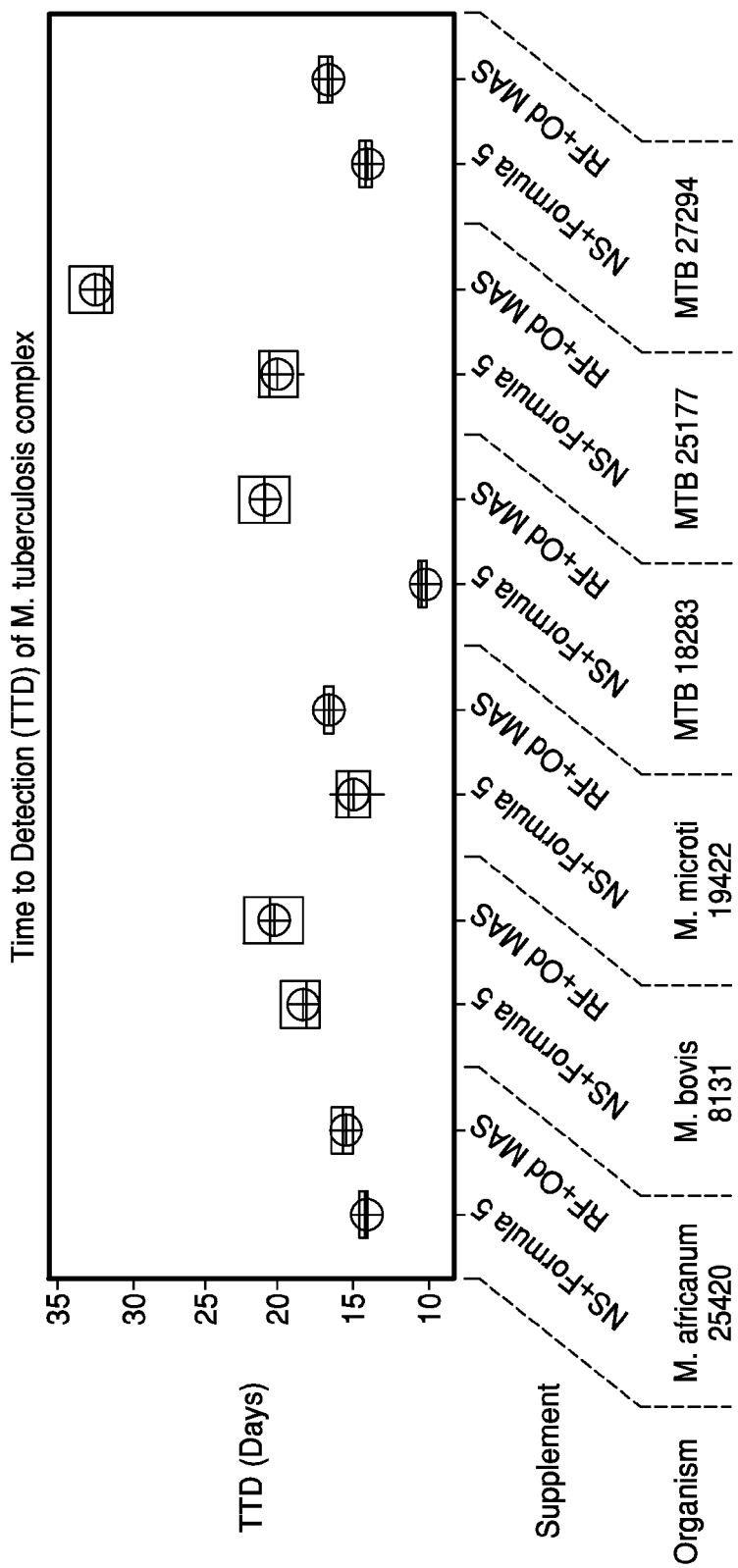

METHOD AND CULTURE MEDIUM FOR ENHANCED DETECTION OF MYCOBACTERIUM

CROSS REFERENCE TO RELATED APPLICATION

This application claims priority as a divisional application of U.S. patent application Ser. No. 12/827,387, which was filed Jun. 30, 2010, is currently pending, and which claims the benefit of U.S. Provisional Patent Application No. 61/269,977, entitled, "Method and Culture Medium for Enhanced Detection of *Mycobacterium*", filed Jul. 1, 2009, which is incorporated herein.

FIELD OF THE INVENTION

The present invention in general is directed to a culture medium and method for enhanced detection of *mycobacterium*. More specifically, the present invention is directed to various improvements to a culture medium and method for improving or reducing the time to detection (TTD) of *mycobacterium* growth in the culture medium.

BACKGROUND OF THE INVENTION

The mycobacteria are a genus of bacteria that are characterized as acid-fast, non-motile, gram-positive bacillus. The genus comprises many species including *Mycobacterium africanum, M. avium, M. bovis, M. bovis*-BCG, *M. chelonae, M. fortuitum, M. gordonae, M. intracellulare, M. kansasii, M. leprae, M. microti, M. scrofulaceum, M. paratuberculosis,* and *M. tuberculosis*. Some of the mycobacteria are pathogenic to both humans and animals, in particular *M. tuberculosis, M. leprae,* and *M. bovis*. Other mycobacterial species are not normally pathogenic, but cause opportunistic infections in immunocompromised individuals, such as AIDS patients. For example, infection by *M. kansasii, M. avium,* and *M. intracellulare* can cause severe lung disease in subjects in whom the immune system is suppressed or compromised. In fact, for the first time since 1953, reported cases of mycobacterial infections are increasing in the United States; many of these cases are related to the AIDS epidemic.

Detection of *Mycobacterium* species in clinical species is important as a clinical diagnostic tool. Historically, *M. tuberculosis* was thought to be the only clinically significant pathogen in this genus. A rise in the incidence of drug-resistant strains of *M. tuberculosis* has further emphasized the need to detect this species. Tuberculosis displays all of the principal characteristics of a global epidemic disease. Currently, tuberculosis afflicts more than 35 million individuals worldwide and results in over 4 million deaths annually. Thus, tuberculosis is a problem of major concern throughout the world. Tuberculosis can be caused by *M. tuberculosis, M. bovis, M. africanum* and *M. microti*, the acid-fast, Gram positive, tubercle bacilli of the family Mycobacteriaceae. Some local pathogenic strains of *M. tuberculosis* have also been isolated from patients in Madras and other cities in India, which differ in some respects from *M. tuberculosis* H37Rv, which is a virulent strain.

Other *Mycobacterium* species, however, are also clinically important. These are sometimes referred to as "MOTT" for *mycobacterium* other than tuberculosis, commonly including *M. avium/intracellulare* complex organisms (*M. avium, M. intracellulare, M. paratuberculosis*, commonly referred to as MAIC), *M. gordonae, M. fortuitum, M. chelonae, M. mucogenicum* and mixtures of *Mycobacterium* species in a clinical specimen. For example, fast-growing opportunistic infections by *M. avium* complex (MAC) bacteria have been shown to occur frequently in AIDS and other immunocompromised individuals. In such infected individuals, at least $10^6$ MAC cells/ml of sputum sediment have been found. Therefore, detection assays that can detect many species of *mycobacterium* are clinically important.

Many clinical methods for detecting and identifying *mycobacterium* species in samples require analysis of the bacteria's physical characteristics (e.g., acid-fast staining and microscopic detection of bacilli), physiological characteristics (e.g., growth on defined media) or biochemical characteristics (e.g., membrane lipid composition). These methods require relatively high concentrations of bacteria in the sample to be detected, may be subjective depending on the clinical technician's experience and expertise, and are time-consuming Because *mycobacterium* species are often difficult to grow in vitro and may take several weeks to reach a useful density in culture, these methods can also result in delayed patient treatment and costs associated with isolating an infected individual until the diagnosis is completed.

Mycobacteria in general, and *M. tuberculosis* and *M. bovis* in particular, are fastidious microorganisms which are very slow growing. It can take two to three weeks to grow these organisms on the culture media conventionally used. There have been several efforts to find a medium or a substance which can enhance the growth and reduce the time factor. For Example, U.S. Pat. No. 3,935,073, which is incorporated herein by reference, discloses a growth medium for culturing mycobacteria containing the following nutrients at the indicated levels: 7H9 broth base 0.47% (containing potassium and sodium phosphates, sodium glutamate, sodium citrate, ammonium sulfate, pyridoxine, ferric ammonium citrate, magnesium sulfate, zinc sulfate, copper sulfate, biotin and calcium chloride obtained from BBL Microbiology Systems in Cockeysville, Md.), bovine serum albumin 0.5%, casein hydrolysate 0.1%, catalase 96 units/vial, $^{14}C$ labeled substrate 2 uCi/vial, deionized water balance to 2 ml, Final pH 6.8±0.1.

Albumin can be used as a detoxifying agent in a medium for the growth of mycobacteria. Albumin is a simple protein found in nearly every animal and in many vegetable tissues. Albumins are characterized as being soluble in water and coagulable by heat. They contain carbon, hydrogen, nitrogen, oxygen and sulfur. A preferred albumin for the growth media of the present invention is bovine serum albumin. The albumin is typically present in the growth media at a level of from about 0.1 percent by weight to about 10 percent by weight.

However, because of the slow growth rate and the need for an enriched medium for mycobacterial growth in culture, detection of mycobacteria from clinical samples (e.g. sputum, lung fluids, tissue or feces) still represents a significant biological challenge. One factor in this challenge arises from the fact that more rapidly-growing bacteria can overgrow the slow-growing mycobacterial organism of interest, thus precluding or significantly hindering mycobacteria detection. Over the decades, several techniques have been developed to decontaminate diagnostic samples (i.e. kill or inhibit non-mycobacterial organisms) submitted for mycobacterial identification. These techniques either kill the potential contaminates or injure them to the extent that their growth is inhibited or totally prevented.

Conventionally, laboratory diagnosis of mycobacteria was based on acid-fast staining and cultivation of the organism, followed by biochemical assays. As a result of the slow growth and long generation time of mycobacteria, accurate laboratory diagnosis of mycobacteria by conventional techniques can take as long as six weeks. Automated culturing systems such as the BacT/ALERT® system (bioMérieux, Inc.) can decrease the time for identification of mycobacteria by up to two weeks.

The present assignee, bioMérieux, Inc. offers the plastic BacT/ALERT® MP culture bottle for use in the BacT/ALERT® Microbial Detection systems as its culture based system for detecting mycobacteria in clinical samples, other than blood. The BacT/ALERT® Microbial Detection System utilizes a colorimetric sensor and reflected light to monitor the presence and production of carbon dioxide ($CO_2$) that is dissolved in the culture medium. If mycobacteria are present in the test sample, carbon dioxide is produced as the microorganisms metabolize the substrates in the culture medium. When growth of the mycobacteria produces $CO_2$, the color of the gas-permeable sensor installed in the bottom of each culture bottle changes from blue-green to yellow.

The BacT/ALERT® MP reagent system includes BacT/ALERT® MP culture bottle, reconstitution fluid (RF) and MB BacT antibiotic supplement (MAS) (hereinafter referred to as conventional or old RF (or conventional/old RF) and conventional or old MAS (or conventional/old MAS). The BacT/ALERT® MP culture bottle is a plastic bottle that contains some components of the medium. The reconstitution fluid (RF) contains the remaining nutrients for mycobacteria growth and is used to reconstitute the MAS. The MAS is a lyophilized powder made up of six antimicrobials to suppress unwanted respiratory flora from sputum samples. The RF and MAS are packaged as the MAS kit. Nevertheless, there still exists a need in the art to further reduce the time required for accurate diagnosis of mycobacteria.

It is, accordingly, a primary object of this invention to provide a culture media and method for enhanced growth and detection of *Mycobacterium* species that may be present in a clinical sample. A further object of this invention is to provide a novel mycobacteria culture medium suitable for the in vitro cultivation of mycobacteria. Still another object of this invention is to provide a mycobacteria culture medium in accordance with the preceding object, wherein growth of contaminating organisms is inhibited.

Accordingly, we describe herein a new culture media formulation, a new nutrient supplement (NS) and a new mycobacterial antimicrobial supplement (MAS) formulation, and manufacturing process improvements that show unexpected enhancement in the growth and detection of mycobacteria. Also described herein are methods for enhanced growth and detection of mycobacteria.

SUMMARY OF THE INVENTION

The present invention generally relates to a novel culture medium for the growth and detection of *Mycobacterium*. Moreover, the present invention provides compositions and diagnostic methods that detect a wide spectrum of *Mycobacterium* species that may be present in a clinical sample. The present invention is also directed to a new and improved MP system or kit that shows enhanced time to detection (TTD) for mycobacterial growth and detection, the MP system or kit comprising an autoclavable BacT/ALERT® MP culture bottle, a nutrient supplement (NS) and a new mycobacteria antimicrobial supplement (MAS).

In one embodiment, the present invention is directed to a novel culture medium for culturing mycobacteria, the culture medium comprising: (a) a base culture medium suitable for growth of mycobacteria; (b) one or more nutrient supplement additives; (c) and an improved antimicrobial supplement; and wherein said culture medium exhibits enhanced growth for said mycobacteria.

In another embodiment, the present invention is directed to a method for enhanced growth of mycobacteria comprising adding a sample suspected of containing mycobacteria to a culture medium containing an effective amount of one or more nutrient additives to enhance the growth of said mycobacteria and subjecting the culture medium to conditions suitable for growth of said mycobacteria.

Another embodiment of the present invention is directed to a method for the diagnosis of infection caused by a *mycobacterium* species, comprising the steps of: (a) providing a culture medium; (b) adding a nutrient supplement to said culture medium, the nutrient supplement comprising one or more nutrient additives for the enhance growth of said mycobacteria; (c) adding a sample for which the presence or absence of said *mycobacterium* species is to be determined, and (d) analyzing the culture for the presence of *mycobacterium* species, wherein a finding of the presence of the *mycobacterium* species indicates a positive diagnosis for said infection.

In still another embodiment, the present invention is directed to an improved BacT/ALERT® MP reagent system or kit. The improved BacT/ALERT® MP reagent system or kit will include an improved MP culture bottle that includes a base culture medium for the growth of mycobacteria or water. Optionally, the culture medium or water of the new MP culture bottle will not include any heat labile components, thereby allowing the new MP culture bottle to be autoclavable. The reagent system or kit will further include a new nutrient supplement (NS) and a new mycobacterial antimicrobial supplement (MAS). The nutrient supplement (NS) may include a base culture medium for the growth of mycobacteria and/or one or more carbon sources, nitrogen sources, sugars, salts, nutrients, proteins, amino acids, fatty acids, or other nutrients.

BRIEF DESCRIPTION OF THE FIGURES

FIG. 1C—is a boxplot showing time to detection (TTD) of *M. avium* with and without fatty acid supplementation.

FIG. 5C—is a boxplot showing time to detection (TTD) of *M. avium* 569 with various mycobacterial antimicrobial supplement (MAS) formulations.

FIG. 5D—is a boxplot showing time to detection (TTD) of *M. intracellulare* 13950 with various mycobacterial antimicrobial supplement (MAS) formulations.

FIG. 6—is a boxplot showing a comparison of the prior MAS formulation versus new mycobacterial antimicrobial supplement (MAS) formulation for time to detection (TTD) of *M. tuberculosis* complex growth.

DETAILED DESCRIPTION OF THE INVENTION

Figure 1A:
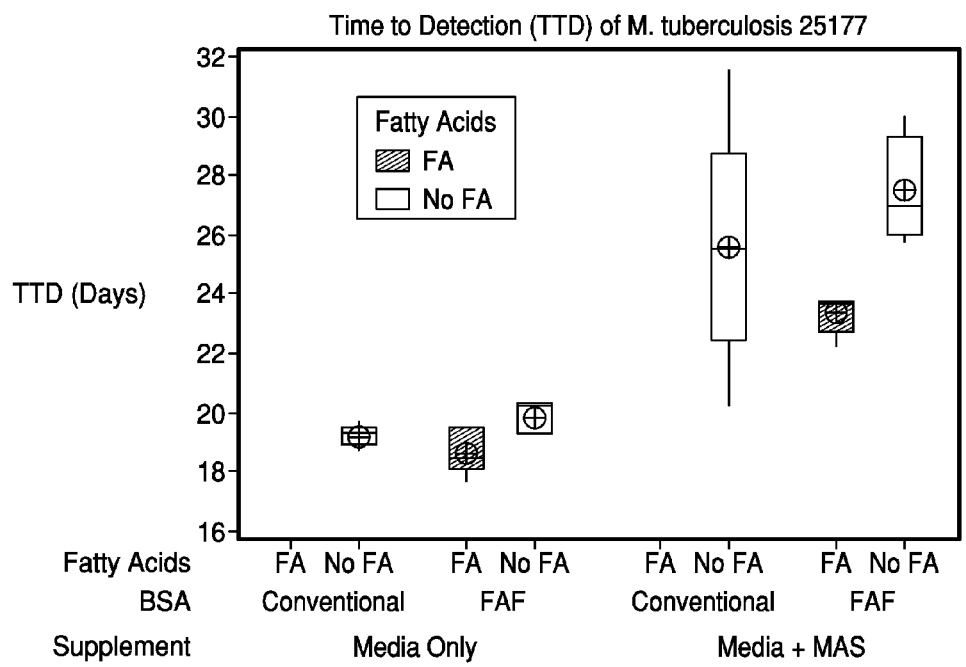
FIG. 1A—is a boxplot showing time to detection (TTD) of *M. tuberculosis* with and without fatty acid supplementation.

The cultivation of propagating microorganisms by providing the proper nutritional and environmental conditions is well known. A suitable growth or culture medium should contain all the nutrients required by the microorganism which is to be cultivated. For example, a typical microbiological culture medium should contain available sources of water, a carbon source, a nitrogen source, vitamins, trace elements such as potassium, magnesium, calcium and iron, and minerals, such as sulfur and phosphorous. Typically, these needs are supplied from a number of sources. Other factors for suitable propagating conditions may include pH, temperature, aeration, salt concentration and osmotic pressure of the medium.

In addition, it is known that certain growth factors may be required. A growth factor is an organic compound which a microorganism must contain in order to grow but which it is unable to synthesize. Many microorganisms, when provided with the nutrients listed above, are able to synthesize all of the organic constituents of their protoplasm, including amino acids, vitamins, purines and pyrimadines, fatty acids and other compounds. Each of these essential compounds is synthesized by a discrete sequence of enzymatic reactions and each enzyme is produced under the control of a specific gene. However, some microorganism cannot synthesis one or more of these growth factors and must then obtain that compound from the environment. Required growth factors may include, but are not limited to, amino acids, vitamins, purines and pyrimadines, fatty acids and other required compounds for growth.

As discussed hereinabove, the current assignee, bioMérieux, Inc., produces and sells a culture media bottle for growth and detection of *mycobacterium* (BacT/ALERT® MP Process Bottle). The BacT/ALERT® MP Process Bottle is designed for use with the BacT/ALERT® or BacT/ALERT® 3D systems for recovery and detection of mycobacteria from sterile body specimens and from digested-decontaminated clinical specimens. The MP Process Bottle can be used in conjunction with the MB/BacT® Antimicrobial Supplement (MAS) and/or the MB/BacT® Reconstitution Fluid (RF) (referred to herein as conventional or old MAS and conventional or old RF).

The BacT/ALERT® MP disposable culture bottle has a removable closure and contains approximately 10 ml of media and an internal sensor that detects carbon dioxide as an indicator of microbial growth. The culture media formulation consists of: Middlebrook 7H9 Broth (0.47% w/v), pancreatic digest of casein (0.1% w/v), bovine serum albumin (0.5% w/v), and catalase (48 u/ml) in purified water (referred to herein as conventional or old media).

The conventional or old MB/BacT® Antimicrobial Supplement (conventional/old MAS) is a lyophilized supplement formulated to contain amphotericin B (0.0180% w/v), azlocillin (0.0034% w/v), nalidixic acid (0.0400% w/v), polymyxin B (10,000 units), trimethoprim (0.00105% w/v), and vancomycin (0.0005% w/v).

The conventional/old MB/BacT® Reconstitution Fluid (conventional/old RF) contains oleic acid (0.05% w/v), glycerol (5% w/v), amaranth (0.004%), and bovine serum albumin (1% w/v) in purified water. The Reconstitution Fluid (RF) and MB BacT/ALERT® Antimicrobial Supplement (MAS) comprise a supplement kit that can be added to the MP bottle.

The present invention is directed to a new and improved culture medium and method for the enhanced growth of *mycobacterium*. The culture medium and methods of the present invention can be used for the cultivation of any known mycobacteria, including, but not limited to, *Mycobacterium tuberculosis*, *Mycobacterium bovis*, *Mycobacterium microti*, *Mycobacterium africanum*, *Mycobacterium canetti*, *Mycobacterium avium*, *Mycobacterium intracellulare*, *Mycobacterium scrofulaceum*, *Mycobacterium kansasii*, *Mycobacterium malmoense*, *Mycobacterium xenopi*, *Mycobacterium marinum*, *Mycobacterium simiae*, *Mycobacterium terrae*, *Mycobacterium ulcerans*, *Mycobacterium abscessus*, *Mycobacterium fortuitum*, *Mycobacterium chelonae*, and *Mycobacterium gordonae*. We have now discovered a new culture media formulation, a new nutrient supplement (referred to herein as new NS) and a new antimicrobial supplement (referred to herein as new MAS) formulation, and manufacturing process improvements that show unexpected enhancement in the growth and detection of mycobacteria.

The novel features of the MP system of the present invention may include: (1) transfer of heat labile components from the MP culture medium to a nutrient supplement, allowing for terminal sterilization of the MP bottle; (2) use of novel carbon sources to optimize $CO_2$ production; (3) optimization of the nutrient supplement; and/or (4) optimization of the MAS antimicrobials and/or concentration of antimicrobials. These improvements lead to several unexpected improvements in the growth and detection of mycobacteria, including: (1) improved performance of the MP bottle in terms of Time To Detection (TTD) of mycobacterial growth; (2) improved recovery of clinically relevant mycobacteria; (3) reduction in breakthrough of contaminating respiratory flora (CRF); and/or (4) minimization of false positives. Additional improvements include simplification of the manufacturing process, such that, BacT/ALERT® MP bottles can be stored and shipped at room temperature.

Culture Medium

In one embodiment, the novel culture medium of the present invention provides for enhanced growth of mycobacteria. As used herein, "enhanced growth" means mycobacteria growth can be detected using the culture medium and/or supplements of the present invention, for example in a culture bottle, at least about 0.5 day, at least about 1 day, at least about 2 days, at least about 3 days, at least about 5 days, or at least about 7 days earlier than using conventional culture media. In other words, mycobacteria growth can be enhanced thereby allowing for an improvement or reduction in time to detection (TTD) of growth compared to the growth of mycobacteria in a conventional culture medium. In accordance with this invention, TTD can be improved or reduced by at least about 0.5 day, at least about 1 day, at least about 2 days, at least about 3 days, at least about 5 days, or at least about 7 days using the culture medium of the present invention compared to conventional culture media. In one embodiment, the conventional culture medium can be the conventional culture media supplemented with the conventional/old RF and conventional/old MAS of the BacT/ALERT® MP Process Bottle (bioMérieux, Inc.), described hereinabove.

In another embodiment, the novel culture medium of the present invention provides for a decrease in lag time for growth of mycobacteria. As used herein, "decreased lag time" means a decrease in the incubation or latency time before the *mycobacterium* enters log phase growth. In accordance with the present invention, the culture medium and/or supplements result in a decrease or reduction of lag time by at least about 0.5 days, or at least about 1 day, or at least about 2 days, or at least about 3 days, when compared to the lag phase of the *mycobacterium* in conventional/old culture medium. In one embodiment, the conventional/old culture medium can be the conventional culture media supplemented with the conventional/old RF and conventional/old MAS of the BacT/ ALERT® MP Process Bottle (bioMérieux, Inc.), described hereinabove.

The culture medium of the present invention comprises a liquid nutrient medium or nutrient broth. The culture medium or nutrient broth of the present invention typically comprises one or more known nutrients, for example, the culture medium may contain one or more carbon sources (e.g., glycerol), nitrogen sources (e.g., ammonia salts), sugars, salts (e.g., $K^+$, $Mg^{2+}$, $Ca^{2+}$, $Zn^{2+}$), nutrients, and/or water. In one embodiment, the culture medium of the present invention comprises Middlebrook 7H9. As discussed hereinabove, Middlebrook 7H9 comprises potassium salts, sodium salts, sodium glutamate, sodium citrate, ammonium sulfate, pyridoxine, ferric ammonium citrate, magnesium sulfate, zinc sulfate, copper sulfate, biotin and calcium chloride.

The culture medium of the present invention may further comprise additional nutrients and/or components that allow for the enhanced detection of mycobacteria growth. Additional nutrients and/or components that may be added to the culture medium of the present invention include, but are not limited to, proteins, amino acids, fatty acids, cell or plant extracts and/or other nutrients. For example, the culture medium of the present invention may further comprise casein (e.g., a pancreatic digest of casein), albumin (e.g., bovine serum albumin), catalase and/or amaranth. In one embodiment, as discussed further herein, these additional nutrients and/or components may comprise a separate nutrient supplement that may be added to a base culture medium prior to the inoculation of the culture medium with a sample for which the determination of the presence or absence of a *mycobacterium* may be desired.

In accordance with the present invention, we have discovered that high levels of short and medium chain fatty acids (e.g., fatty acids having about 8 or fewer carbon atoms) associated with bovine serum albumin (BSA) in the culture media bottle may result in false positive readings. As such, it may be preferred to avoid using short, or medium chain fatty acids. For example, in accordance with this embodiment, the use of fatty acids having 8 or fewer carbon atoms (e.g., caprylic acid) should be avoided.

However, we have also discovered that these reagent induced false positives can be eliminated or significantly reduced by using fatty acid free BSA and supplementing the culture medium formulation with long chain fatty acids. Accordingly, the culture medium may further comprise fatty acid free BSA (FA-free BSA) and one or more saturated or unsaturated long chain fatty acids, or salts thereof. In one embodiment, it may be preferred to utilize one or more long chain fatty acids having 10 or more carbon atoms. In general, any known long chain fatty acid can be used, including, but not limited to, myristic acid, palmitic acid, stearic acid, oleic acid, linoleic acid, and salts thereof. In another embodiment, as discussed further herein, we have found that the fatty acids can be transferred from the culture media of the bottle to a nutrient supplement that can be added separately to the culture media prior to inoculation with a test sample. As shown herein (see, e.g., Example 1 and FIGS. 1A-1C), the use of a fatty acid free BSA and supplementation of the culture medium with long chain fatty acids resulted in an improvement in time to detection (TTD) of 2 to 2.5 days for the growth and detection of *M. tuberculosis* (see FIG. 1A), *M. intracellulare* (see FIG. 1B), and *M. avium* (see FIG. 1C).

In one aspect of the present invention, the culture medium of the present invention can be supplemented with one or more known metabolic pathway substrates or intermediates. We surprisingly discovered that by including a metabolic pathway substrate (e.g., α-ketoglutarate) in the culture media, mycobacteria growth and detection could be enhanced compared to a culture media not containing the metabolic pathway substrate (e.g., α-ketoglutarate). Although not wishing to be bound by theory, it is believe that the use of a metabolic pathway substrate (e.g., α-ketoglutarate) in the culture medium may enhance $CO_2$ production by mycobacteria present in the culture. In accordance with this embodiment, substrates or intermediates of the citric acid cycle, glycolysis or glyoxylate bypass can be used. In one embodiment, substrates or cofactors of $CO_2$ producing enzymes, or intermediates, precursors or derivatives thereof, may be used in the present invention. For example, citric acid cycle intermediates, such as pyruvate, citrate, cis-aconitate, isocitrate, oxalosuccinate, α-ketoglutarate, succinyl-CoA, succinate, fumarate, malate, oxaloacetate, may be useful. In another embodiment, one or more of α-ketoglutarate, an α-ketoglutarate precursor, and/or an α-ketoglutarate derivative can be included in the culture medium of the present invention. The α-ketoglutarate precursors or derivatives, may include, but are not limited to, glutamate, isocitrate, oxalosuccinate, or mixtures thereof. The α-ketoglutarate, α-ketoglutarate precursor(s), and/or α-ketoglutarate derivative(s) can be present in the culture medium at a final concentration of from about 0.1 g/L to about 50 g/L, from about 0.5 g/L to about 20 g/L, or from about 1 g/L to about 20 g/L. In one embodiment, as discussed further herein, the α-ketoglutarate, α-ketoglutarate precursor, and/or α-ketoglutarate derivative can be included in a nutrient supplement that can be added separately to the culture media.

In yet another aspect of the present invention, the culture medium of the present invention may further comprise one or more antimicrobial agents or substances. An antimicrobial is an agent or substance that kills, suppresses, or otherwise inhibits the growth of microbes. In general, any known antimicrobial agent can be used, such as, drugs, chemicals, or other substances that kill, suppress, or slow the growth of microbes. Useful antimicrobial agents include, but are not limited to, antibiotics, bacteriostatics, bactericides, antibacterials, antivirals, antifungals, antiprotozoals and antiparasites. In general, the antimicrobial is used at an amount sufficient to kill, suppress, or inhibit the growth of contaminating bacteria which may be present in the culture medium. For example, as one of skill in the art would understand, it may be preferred to inhibit the growth of contaminating respiratory flora (CRF) in the culture medium. CRF can interfere with the growth of mycobacteria, deplete necessary nutrients for mycobacterial growth and/or lead to false positives. Contaminating respiratory flora (CRF) may include, but are not limited to, *P. aeruginosa, S. aureus, C. albicans, E. faecalis, K. pnuemoniae, S. maltophilia, C. tropicalis*, methicillin resistant *S. aureus* (i.e., MRSA), vancomycin resistant *E. faecalis* (i.e., VRE).

The antimicrobial may be one or more antibiotics or synthetic drugs, including, but not limited to, polymyxin B, vancomycin, azlocillin, amphotericin B, nalidixic acid, trimethoprim and fosfomycin. In a preferred embodiment, useful antibiotics inhibit contaminating respiratory flora (CRF) without suppressing or inhibiting mycobacterial growth.

In some embodiments, the antimicrobial supplement comprises one or more antifungal antibiotics, gram negative antibiotics, gram positive antibiotics, an antifungal antibiotic, and broad-spectrum antibiotics. For example, the antimicrobial supplement of the present invention may comprise, an antifungal (e.g., amphotericin B), a gram-negative antibiotic that alters the cytoplasmic membrane permeability (e.g., polymyxin B), a broad-spectrum antibiotic that inhibits DNA gyrase (e.g., nalidixic acid), a chemotherapeutic agent (e.g., an agent that inhibits dihydrofolate reductase (e.g., trimethoprim)) and a broad-spectrum antibiotic that inhibits enolpyruvate transferase (e.g., fosfomycin). In general, any known antifungals, gram negative antibiotics, broad-spectrum antibiotics, antibiotic inhibitors of DNA Gyrase, or chemotherapeutic agent, can be used in the practice of this invention. In one embodiment, the antimicrobial supplement may comprise amphotericin B, polymyxin B, nalidixic acid, trimethoprim and fosfomycin.

As shown herein (see, e.g., Examples 3-4 and FIGS. 3-4), the use of vancomycin and/or azlocillin may suppress, inhibit or slow the growth of some mycobacteria species. Thus, in some embodiments, it may be preferred to avoid the use of vancomycin and/or azlocillin. We have discovered that fosfomycin can be used instead of azlocillin and vancomycin to yield an antimicrobial supplement (MAS) that can be used to enhance growth and detection of mycobacteria in culture, when compared to the MB/BacT® Antimicrobial Supplement. For example, by replacing azlocillin and vancomycin with fosfomycin, we have found the new mycobacterial antimicrobial supplement (MAS) improves or reduces the time to detection (TTD) of mycobacteria growth from 2-9 days, when compared to the conventional/old MAS (see, e.g., Example 5 and FIGS. 5A-5F). Therefore, in some embodiments, the use of polymyxin B, amphotericin B, nalidixic acid, trimethoprim and fosfomycin may be preferred. These antibiotics can be used in amounts sufficient to inhibit the growth of contaminating bacteria which may be present in the culture medium. For example, the culture medium may contain a final concentration of from about 400 units/ml to about 2000 units/ml polymyxin B, from about 50 µg/ml to about 400 µg/ml amphotericin B, from about 100 µg/ml to about 1000 µg/ml nalidixic acid, from about 10 µg/ml to about 100 µg/ml trimethoprim and from about 100 µg/ml to about 1000 µg/ml fosfomycin. In one embodiment, as discussed further herein, these antimicrobial agents may comprise a separate supplement that may be added to a base culture medium prior to the inoculation of the culture medium with a sample for which the determination of presence or absence of a *mycobacterium* may be desired.

In accordance with the present invention, in one embodiment, the culture medium of the present invention may comprise one or more of Middlebrook 7H9, bovine serum albumin, α-ketoglutarate, casein, catalase, and/or water. The culture medium may further comprise one or more additional nutrients and/or components known to those of skill in the art as being beneficial to the cultivation of mycobacteria. For example, the culture medium of the present invention may additionally comprise of one or more sugars or carbon sources, nitrogen sources, minerals, salts, amino acids, vitamins, purines and pyrimadines, fatty acids and other compounds. In another embodiment, the culture medium of the present invention comprises Middlebrook 7H9, glycerol, stearic acid (e.g., sodium stearate), myristic acid (or salt thereof), palmitic acid (e.g., sodium palmitate), oleic acid (e.g., sodium oleate), bovine serum albumin, casein (e.g., pancreatic digest of casein), catalase, sodium pyruvate, α-ketoglutarate, amaranth and water.

In yet another embodiment, the culture medium further comprises one or more antimicrobial agents (e.g., fosfomycin). For example, the culture medium may further comprises a mixture of antimicrobial agents, selected from one or more of polymyxin B, azlocillin, vancomycin, amphotericin B, nalidixic acid, trimethoprim and/or fosfomycin. The culture medium may further comprise a mixture of antibiotics comprising polymyxin B, amphotericin B, nalidixic acid, trimethoprim and fosfomycin.

In still another embodiment, the culture medium can be adjusted to a pH of from about 5.5 to about 7.5, a pH of from about 6.0 to about 7.0, or a pH of from about 6.5 to about 7.0. In accordance with this invention, the culture medium improves or reduces the time to detection (TTD) of mycobacterial growth by at least about 0.5, at least about 1, at least about 2, at least about 3, at least about 5, or at least about 7 days compared to conventional/old mycobacterial culture medium.

Method for Enhanced Detection of Mycobacteria

In general, the present invention is also directed to a method for detecting the growth of one or more *mycobacterium* that may be present in a biological sample. Samples that may be tested include both clinical and non-clinical samples where the presence of a *mycobacterium* may be suspected. Clinical samples that may be tested include any type of sample typically tested in clinical laboratories, including, but not limited to, blood, sputum, aspirates, swabs and swab rinsates, other body fluids, and the like. In one embodiment, the sample may be a sterile body specimen or a digested-decontaminated clinical specimen. Non-clinical samples that may be tested also include highly variable substances, encompassing, but not limited to, foodstuffs, beverages, pharmaceuticals, cosmetics, water, air, soil, plants, blood products (including platelets), donor organ or tissue samples, and the like.

In one aspect, the present invention is directed to a method for enhanced growth and/or detection of mycobacteria comprising adding a sample suspected of containing mycobacteria to a culture medium comprising fatty acid-free BSA, one or more long chain fatty acids, and optionally an antimicrobial supplement, and subjecting the culture medium to conditions suitable for growth of said mycobacteria, wherein said fatty acid-free BSA and said one or more long chain fatty acids enhance the growth of said mycobacteria. We have found that the use of fatty acid-free BSA and one or more long chain fatty acids in the NS results in a substantial reduction in false positive readings. Furthermore, as shown herein (see Example 1 and FIGS. 1A-1C), the use of a fatty acid free BSA and supplementation of the culture medium with long chain fatty acids resulted in an improvement in time to detection (TTD) of 2 to 2.5 days for the growth and detection of *M. tuberculosis* (see FIG. 1A), *M. intracellulare* (see FIG. 1B), and *M. avium* (see FIG. 1C). In one embodiment, the culture medium may further comprise an effective amount of an additive comprising α-ketoglutarate, an α-ketoglutarate precursor or an α-ketoglutarate derivative to enhance the growth of said mycobacteria and subjecting the culture medium to conditions suitable for growth of said mycobacteria. We have unexpectedly discovered that by using α-ketoglutarate, an α-ketoglutarate precursor and/or an α-ketoglutarate derivative in the culture medium and method of the present invention that the time to detection (TTD) of mycobacterial growth can be detected at least about 0.5 day, at least about 1 day, at least about 2 days, at least about 3 days, at least about 5 days, or at least about 7 days earlier than using conventional/old culture medium (i.e., culture medium not having α-ketoglutarate, an α-ketoglutarate precursor or derivative). As shown in Example 2 and FIG. 2, the time to detection (TTD) of mycobacteria strains in a culture medium containing α-ketoglutarate is improved or reduced by approximately two days compared to TTD in a culture medium not containing α-ketoglutarate.

The present invention is also directed to a method for the diagnosis of infection caused by a *mycobacterium* species, comprising the steps of: (a) providing a culture medium; (b) adding a nutrient supplement to said culture medium, said nutrient supplement additive comprising fatty acid-free BSA and optionally one or more long chain fatty acids; (c) adding a sample for which the presence or absence of said *mycobacterium* species is to be determined; and (d) analyzing said culture for the presence of said *mycobacterium* species, wherein a finding of the presence of said *mycobacterium* species indicates a positive diagnosis for said infection. We have found that the use of fatty acid-free BSA and one or more long chain fatty acids in the NS results in a substantial reduction in false positive readings. Furthermore, as shown herein (see Example 1 and FIGS. 1A-1C), the use of a fatty acid free BSA and supplementation of the culture medium with long chain fatty acids resulted in an improvement in time to detection (TTD) of 2 to 2.5 days for the growth and detection of *M. tuberculosis* (see FIG. 1A), *M. intracellulare* (see FIG. 1B), and *M. avium* (see FIG. 1C). In one embodiment, the supplement may further comprise α-ketoglutarate, an α-ketoglutarate precursor and/or an α-ketoglutarate derivative. As discussed hereinabove, the use of α-ketoglutarate, an α-ketoglutarate precursor or an α-ketoglutarate derivative in the culture medium and method of the present invention can reduce the TTD by at least about 0.5 day, at least about 1 day, at least about 2 days, at least about 3 days, at least about 5 days, or by at least about 7 days. In accordance with this method, the nutrient supplement (NS) may optionally use fatty acid-free BSA and further comprise one or more long chain fatty acids (e.g., fatty acids having 10 or more carbon atoms).

In another embodiment, the present invention is directed to a method of inhibiting bacterial contamination in a mycobacteria culture, the method comprising culturing a sample suspected of containing mycobacteria in a culture medium comprising fosfomycin in an amount sufficient to inhibit the growth of contaminating bacterium under conditions suitable for growth of said mycobacteria. In accordance with this method, one or more antimicrobial agents or substances can be added to the culture medium prior to, or concurrently with inoculation of the culture medium with the biological sample to be tested. Subsequently, the culture media and sample can be cultivated for a sufficient time and at a sufficient temperature to allow for the growth and detection of any mycobacteria that may be present in the test sample. In another embodiment, the one or more antimicrobials can be included in a mycobacterial antimicrobial supplement (MAS) that can be added to the base culture medium prior to, or concurrently with inoculation of the culture medium with the sample to be tested. As described hereinabove, the MAS may comprise of one or more of polymyxin B, amphotericin B, nalidixic acid, trimethoprim, and fosfomycin.

In still another embodiment, the present invention is directed to method employing the use of an improved BacT/ALERT® MP reagent system or kit for the growth and/or detection of mycobacteria that may be present in a biological sample. In accordance with this embodiment, as described in further detail herein, the improved BacT/ALERT® MP reagent system will include an improved MP culture bottle that includes a base culture medium for the growth of mycobacteria, a new nutrient supplement (NS) and a new mycobacterial antimicrobial supplement (MAS). The nutrient supplement (NS) and/or mycobacterial antimicrobial supplement (MAS) can be added to the base culture medium of the bottle prior to, or concurrently with inoculation of the culture medium with the biological sample to be tested for the presence of mycobacteria. The inoculated bottle will be cultivated for a sufficient time and at a sufficient temperature to allow for growth and/or detection of any mycobacteria that may be present in the biological sample. In one embodiment, the culture medium of the new MP culture bottle will not include any heat labile components, thereby allowing the new MP culture bottle to be autoclavable.

MP Reagent Kit

In one aspect, the present invention is directed to an MP reagent kit for the enhanced growth and detection of mycobacteria. The MP reagent kit will include a culture bottle having a base *mycobacterium* culture medium, a nutrient supplement (NS), and/or a mycobacterial antimicrobial supplement (MAS).

Culture Bottle

In one embodiment, the present invention is directed to a bottle or container (i.e., a culture bottle) that contains a new and improved *mycobacterium* culture medium. In general, the culture bottle may be of any design or size known in the art, and may comprise any known culture medium beneficial to the growth and/or detection of mycobacteria. In one embodiment, the culture bottle comprises Middlebrook 7H9 broth and/or water as a base culture medium. The conventional/old MP bottle uses a liquid culture media with a pH of about 6.8 for the growth and detection of *Mycobacterium*. Likewise, the new and improved MP culture bottle will have a liquid or broth base culture medium to which a new nutrient supplement and/or a new mycobacterial antimicrobial supplement (MAS) can be added. The culture medium can be adjusted to a pH of from about 5.5 to about 7.5, a pH of from about 6.0 to about 7.0, or a pH of from about 6.5 to about 7.0. In another embodiment, the MP culture bottle culture medium will have a pH of about 6.8.

We have surprisingly found that by removing certain growth nutrients from the culture media bottle, including, for example, bovine serum albumin, catalase bovine liver and/or casein, the bottle can be terminally sterilized. For example, by removing the heat labile components the bottle can be autoclaved. Improvements related to terminal sterilization of the bottle include improved storage and shipping. For example, the terminally sterilized bottle (e.g., autoclaved bottle) can be stored and shipped at room temperature resulting in considerable cost reduction. The terminally sterilized bottle may further result in an improved shelf life and/or an increased sterility level (SAL).

Nutrient Supplement (NS)

The present invention is also directed to an improved nutrient supplement (NS) that can be added to the culture bottle of the present invention to enhance the growth and detection of mycobacteria. In general, the nutrient supplement (NS) is added to a culture bottle containing a base culture medium for mycobacteria growth, prior to inoculation of the bottle and culture medium with a sample for which detection of the presence of a *mycobacterium* is desired.

The improved nutrient supplement (NS) of the present invention can include any known nutrient or supplement beneficial to the growth of mycobacteria. For example, the nutrient supplement may include one or more carbon sources, nitrogen sources, sugars, salts, nutrients, proteins, amino acids, fatty acids, and/or other nutrients known to those skilled in the art.

In accordance with this invention, in one embodiment, the nutrient supplement may further comprise α-ketoglutarate, an α-ketoglutarate precursor and/or an α-ketoglutarate derivative. In general, any known α-ketoglutarate precursor or derivative can be used, including, but not limited to, glutamate, isocitrate, oxalosuccinate, or mixtures thereof. The α-ketoglutarate, α-ketoglutarate precursor(s), and/or α-ketoglutarate derivative(s) can be present in the nutrient supplement at a sufficient amount such that after addition to the culture medium of the culture bottle, the final concentration of α-ketoglutarate, α-ketoglutarate precursor and/or α-ketoglutarate derivative is from about 0.1 g/L to about 50 g/L.

In accordance with another embodiment of the present invention, the nutrient supplement may further comprise one or more saturated or unsaturated long chain fatty acids, or salts thereof, one embodiment, it may be preferred to utilize one or more long chain fatty acids having 10 or more carbon atoms. In general, any known long chain fatty acid can be used, including, but not limited to, myristic acid, palmitic acid, stearic acid, oleic acid, linoleic acid, and salts thereof. In another embodiment, it may be preferred to avoid using short, or medium chain fatty acids. For example, in accordance with this embodiment, the use of fatty acids having 8 or fewer carbon atoms (e.g., caprylic acid) should be avoided.

In another aspect, as mentioned hereinabove, it may be preferred to use fatty acid free bovine serum albumin (BSA) in the nutrient supplement of the present invention. As previously mentioned, the use of fatty acid free BSA can substantially reduce or eliminate reagent based false positives.

In one embodiment, the nutrient supplement (NS) comprises glycol, one or more long chain fatty acids, fatty acid free bovine serum albumin (BSA), pancreatic digest of casein, sodium pyruvate, amaranth and α-ketoglutarate. The nutrient supplement can be added to the culture bottle along with the base culture medium, or can be added to the culture bottle just prior to inoculation with a test sample. Alternatively, the nutrient supplement can be used to resuspend the mycobacterial antimicrobial supplement (MAS) and then added to the culture media bottle.

Mycobacterial Antimicrobial Supplement (MAS)

The present invention is also directed to an improved mycobacterial antimicrobial supplement (MAS) that can be added to the culture bottle of the present invention to enhance the growth and detection of mycobacteria. We have developed an improved mycobacterial antimicrobial supplement (MAS) that enhances the growth of mycobacteria in culture. The improved MAS is effective in suppressing or inhibiting the growth of contaminating respiratory flora (CRF) without suppressing or inhibiting mycobacterial growth. Contaminating respiratory flora (CRF) may include, but are not limited to, *P. aeruginosa, S. aureus, C. albicans, E. faecalis, K. pnuemoniae, S. maltophilia, C. tropicalis*, methicillin resistant *S. aureus* (MRSA), vancomycin resistant *E. faecalis* (VRE). In one embodiment, the mycobacterial antimicrobial supplement (MAS) can be directly added to a culture bottle comprising a base culture medium for mycobacteria growth, prior to inoculation of the bottle and culture medium with a sample for which detection of the presence of a *mycobacterium* is desired. In another embodiment, the nutrient supplement (NS) can be used to resuspend the antimicrobial supplement (MAS), prior to being added to the culture media bottle.

In general, any known antimicrobial agent or substance may be used, including, but not limited to, antibiotics, bacteriostatics, bactericides, antibacterials, antivirals, antifungals, antiprotozoals and/or antiparasites. However, preferred antimicrobial agents include any antimicrobials that suppress or inhibit the growth of contaminating respiratory flora (CRF) without suppressing or inhibiting the growth of mycobacteria. In one embodiment, the MAS comprises one or more antimicrobials in an amount sufficient to inhibit bacterial contamination in said culture medium.

In another embodiment, the culture medium of the present invention includes one or more antibiotics. Useful antibiotics include, for example, antibiotics the suppress or inhibit CRF growth, including, but not limited to, polymyxin B (POLY B), vancomycin (VAN), azlocillin (AZL), amphotericin B (AMP B), nalidixic acid (NA), trimethoprim (TMP) and fosfomycin (FOS). Antibiotics used to treat mycobacterial infections and which may kill, suppress or inhibit mycobacteria growth are not useful in the antibiotic supplement in the present invention and include, for example, isoniazid, rifampin, pyrazinamide, streptomycin and ethambutol. As previously discussed hereinabove, the present assignee markets and sells a MB/BacT® Antimicrobial Supplement that is a lyophilized supplement formulated to contain amphotericin B (0.0180% w/v), azlocillin (0.0034% w/v), nalidixic acid (0.0400% w/v), polymyxin B (10,000 units), trimethoprim (0.00105% w/v), and vancomycin (0.0005% w/v). However, we have now unexpectedly discovered that fosfomycin can be supplemented for azlocillin and vancomycin to yield an antimicrobial supplement (MAS) that can be used for the enhanced growth and detection of mycobacteria in culture, when compared to the conventional/old MB/BacT® Antimicrobial Supplement.

As such, in one embodiment, the improved mycobacterial antimicrobial supplement (MAS) comprises a lyophilized supplement formulated to contain ampotericin B (AMP B), polymyxin B (POLY B), trimethoprim (TMP), nalidixic acid (NA) and fosfomycin (FOS). The mycobacterial antimicrobial supplement (MAS) can be formulated such that the final culture medium will contain a final concentration of from about 400 units/ml to about 2000 units/ml polymyxin B, from about 50 μg/ml to about 400 μg/ml amphotericin B, from about 100 μg/ml to about 800 μg/ml nalidixic acid, from about 10 μg/ml to about 100 μg/ml trimethoprim and from about 100 μg/ml to about 1000 μg/ml fosfomycin.

In yet another embodiment, the nutrient supplement (NS) and antimicrobial supplement (MAS) may form a separate kit that can then be added to a terminally sterilized culture media bottle. In this embodiment, the NS/MAS kit can be separately marketed and sold as an additive for the BacT/ALERT MP bottle.

The following examples are given to further illustrate features of the invention, but are not intended to limit the scope of the invention in any way.

EXAMPLES

Example 1

TTD of Various Mycobacteria Strains with and without Fatty Acid Supplementation

To evaluate the effect of long chain fatty acids (FA) on Mycobacteria growth, fatty acid free (FAF) BSA was selected from Proliant, Inc. (Ames, Iowa). Five long chain FA: myristic acid (C14:0), palmitic acid (C16:0), stearic acid (C18:0), oleic acid (C18:1), and linoleic acid (C18:2) were identified as possible FA supplements based on the FA profile and growth performance. A new formulation of supplement with FAF BSA was prepared and tested with and without the five FA (see Table 1 for new supplement formulation). The FA supplementation target levels were based on FA content obtained from previous evaluations. The FAF BSA concentration used was 10 g/L. The loss of FA during filtration of new supplement was determined by Fatty Acid Methyl Ester (FAME) analysis. The recovery of FA was observed to be >80% after filtration with 0.45 µm filter. The analysis of this formulation demonstrated that the higher levels of BSA enhanced the FA solubilization and stability by BSA-FA binding (data not shown). The analysis also demonstrated that the lower the BSA content, the less binding of FA resulting in more FA loss during filtration.

A new autoclavable culture bottle was devised by transferring heat labile components of culture medium present in the conventional or old bottle to the conventional/old RF. The new autoclavable culture bottle comprised Middlebrook 7H9. The new RF supplement was prepared using the composition of conventional or old RF but modifying to accommodate the heat labile components transferred from the old MP bottle formulation. Table 1 below shows the composition of a new autoclavable MP bottle (as described hereinabove) and new supplement. BSA used in this new supplement was fatty acid free (FAF) BSA (Proliant Inc., Ames, Iowa) rather than conventional BSA used in conventional/old RF.

TABLE 1

New MP Bottle and New Supplement formulations

New MP Bottle
MP Culture Bottle

| Raw Material | g/L |
|---|---|
| Middlebrook 7H9 | 4.7 |

Modified RF or New Supplement
Reconstitution Fluid

| Raw Material | g/L |
|---|---|
| Bovine Serum Albumin | 210 |
| Pancreatic digest or Casein | 20 |

TABLE 1-continued

New MP Bottle and New Supplement formulations

| Catalse Bovine Liver | 0.86 |
|---|---|
| Glycerol | 50 |
| Oleic acid | 0.475 |
| Sodium pyruvate | 20 |
| Amaranth | 0.04 |

For Growth Performance, five organisms (*M. tuberculosis*, *M. avium*, and *M. intracellulare*) were tested. The conventional MAS formulation was used for these experiments. The new supplement with/without FA supplementation and conventional/old RF were used to rehydrate a lyophilized powder of the conventional or old MB BacT antibiotic supplement (conventional/old MAS) (bioMérieux, Inc.). The conventional/old MAS contained 1000 units/ml polymyxin B (POLY B), 180 µg/ml amphotericin B (AMP B), 400 µg/ml nalidixic acid (NA), 10.5 µg/ml trimethoprim (TMP), 34 µg/ml Azlocillin (AZL) and 5 µg/ml Vancomycin (VAN).

For the new supplement, the new, autoclavable BacT/ALERT® MP bottle (as described hereinabove) was used and for conventional/old RF, the conventional/old MP bottle was used. Before the inoculation of new and conventional/old MP culture bottles (bioMérieux, Inc.) with mycobacteria cultures, 0.5 ml of new supplement with/without FA or 0.5 ml of conventional/old RF were added to one set of the BacT/ALERT® MP culture bottles. The rehydrated conventional MAS (using new supplement with/without FA and conventional/old RF) was added to the second set of MP culture bottles. The growth (as TTD of growth) was compared in these bottles for *Mycobacterium avium*, *Mycobacterium intracellulare* and *Mycobacterium tuberculosis* cultures after inoculating with approximately $0.5 \times 10^3$ CFU/ml. The colony counts were also performed using Middlebrook 7H10 agar plates to verify the inoculum levels and purity of cultures. The inoculated MP bottles were loaded at 35-37° C. in BacT/ALERT® 3D (bioMérieux, Inc.) non-rocking system for 35 days. Time To Detection (TTD) data was collected when the bottles were declared positive by the BacT/ALERT® instrument. The results are shown in Table 2 and FIGS. 1A-1C.

TABLE 2

TTD results for *M. tuberculosis*, *M. intracellulare* and *M. avium*

| Organism | Supplement | BSA | Fatty Acids | Avg. TTD | Std. Dev. TTD | Min. TTD | Max. TTD | # Positive | # Tested |
|---|---|---|---|---|---|---|---|---|---|
| *M. avium* 25291 | Media only | Conventional | No FA | 15.1 | 0.7 | 14.3 | 16.0 | 5 | 5 |
| | | FAF | FA | 15.3 | 0.5 | 14.8 | 15.8 | 5 | 5 |
| | | | No FA | 17.0 | 0.6 | 16.2 | 17.7 | 5 | 5 |
| | Media + MAS | Conventional | No FA | 18.1 | 0.9 | 16.7 | 19.0 | 5 | 5 |
| | | FAF | FA | 16.8 | 0.9 | 15.8 | 17.7 | 5 | 5 |
| | | | No FA | 21.0 | 0.8 | 20.3 | 22.0 | 5 | 5 |
| *M. intracellulare* 13950 | Media only | Conventional | No FA | 8.3 | 0.3 | 7.8 | 8.7 | 5 | 5 |
| | | FAF | FA | 7.9 | 0.3 | 7.5 | 8.2 | 5 | 5 |
| | | | No FA | 12.5 | 0.5 | 11.7 | 12.8 | 5 | 5 |
| | Media + MAS | Conventional | No FA | 18.7 | 2.7 | 16.0 | 22.5 | 5 | 5 |
| | | FAF | FA | 13.8 | 1.4 | 11.5 | 16.0 | 10 | 10 |
| | | | No FA | 24.8 | 6.1 | 17.3 | 33.5 | 10 | 10 |
| MTB 25177 | Media only | Conventional | No FA | 19.3 | 0.4 | 18.7 | 19.7 | 5 | 5 |
| | | FAF | FA | 18.7 | 0.8 | 17.7 | 19.5 | 5 | 5 |
| | | | No FA | 19.9 | 0.5 | 19.3 | 20.3 | 5 | 5 |
| | Media + MAS | Conventional | No FA | 25.6 | 4.0 | 20.2 | 31.5 | 5 | 5 |
| | | FAF | FA | 23.4 | 0.6 | 22.3 | 23.8 | 5 | 5 |
| | | | No FA | 27.6 | 1.8 | 25.8 | 30.0 | 5 | 5 |

Figure 2:
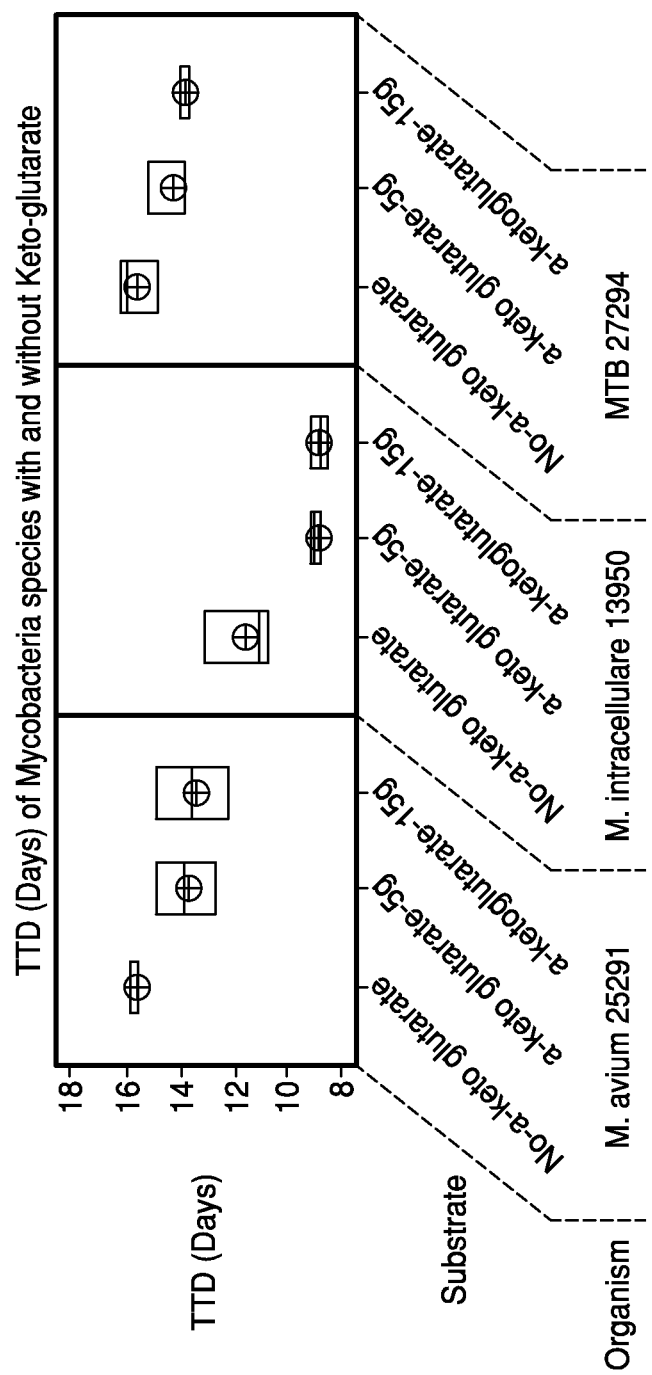
FIG. 2—is a boxplot showing time to detection (TTD) of mycobacteria strains with and without α-ketoglutarate.

FIG. 1A shows TTD results for *Mycobacterium tuberculosis* in cultures containing FA free (FAF) BSA with and without supplementation of long chain fatty acids. As shown in FIG. 1A, a reduction in TTD was seen in samples containing FA free BSA supplemented with FAs when compared to samples containing BSA without supplementation of FA.

Figure 1B:
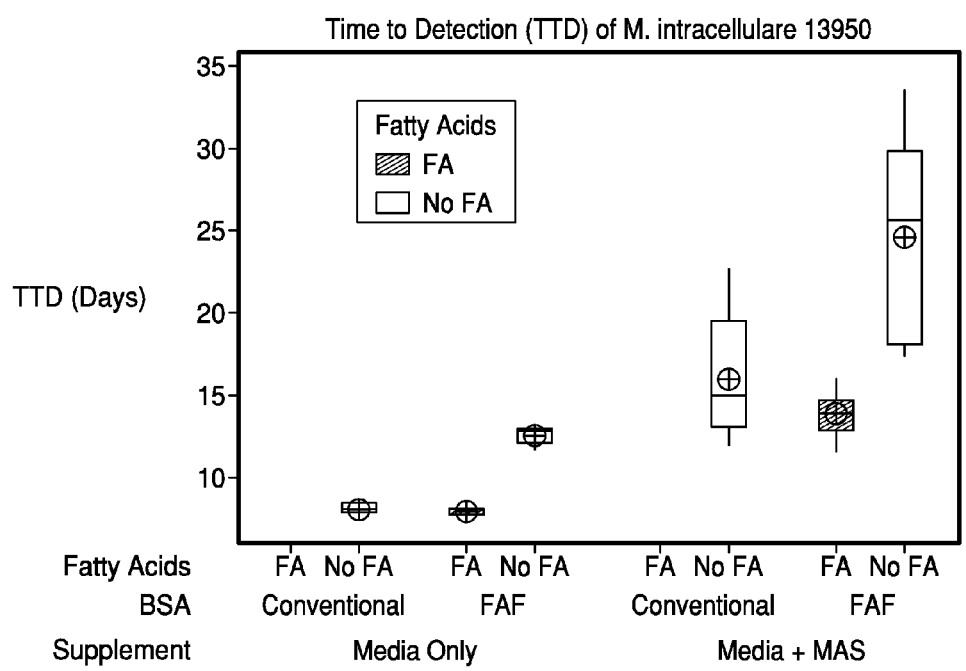
FIG. 1B—is a boxplot showing time to detection (TTD) of *M. intracellulare* with and without fatty acid supplementation.

FIG. 1B shows TTD results for *Mycobacterium intracellulare* in cultures containing FA free (FAF) BSA with and without supplementation of long chain fatty acids. As shown in FIG. 1B, a reduction in TTD was seen in samples containing FA free BSA supplemented with FAs when compared to samples containing BSA without supplementation of FA.

FIG. 1C shows TTD results for *Mycobacterium avium* in cultures containing FA free (FAF) BSA with and without supplementation of long chain fatty. As shown in FIG. 1C, a reduction in TTD was seen in samples containing FA free BSA supplemented with FAs when compared to samples containing BSA without supplementation of FA.

The results demonstrated an improvement in TTD of *M. tuberculosis*, *M. intracellulare*, and *M. avium* by 2 to 2.5 days in the presence of mycobacterial antimicrobial supplement (MAS) and new nutrient supplement (NS). As discussed hereinabove, the new NS comprises fatty acid free BSA and supplemented long chain fatty acids.

Example 2

TTD of Mycobacteria Strains with and without α-Ketoglutarate

To improve TTD of mycobacteria further, substrates and/or cofactors of $CO_2$-producing enzymes in the mycobacterial cell pathways were selected for further study, including α-ketoglutarate, iso-citrate, L-malate, oxaloacetic acid, lactate and L-arginine. The new supplement with FA was prepared and filter sterilized as explained above. The substrates were added at different concentrations in the new supplement.

Four species of mycobacteria were tested at $0.5\times10^3$ CFU/ml. The effect of different concentrations of α-ketoglutarate was studied on the growth (as TTD of growth) of *Mycobacterium avium, Mycobacterium intracellulare* and *Mycobacterium tuberculosis* cultures. A new, autoclavable BacT/ALERT® MP culture bottle was used (as described hereinabove). Before the inoculation of MP culture bottles with mycobacteria cultures, 0.5 ml of new supplement with various amounts of α-ketoglutarate was added to the new BacT/ALERT® MP culture bottles. The colony counts were also performed using Middlebrook 7H10 agar plates to verify the inoculum levels and purity of cultures. The inoculated MP bottles were loaded at 35-37° C. in BacT/ALERT® 3D non-rocking system for 35 days. Time To Detection (TTD) data was collected when the bottles were declared positive by the BacT/ALERT® instrument.

The results for TTD of key mycobacteria species with the inclusion of two concentrations of α-ketoglutarate 5 and 15 g/L are presented in Table 3 and FIG. 2. Table 3 and FIG. 2 show that the addition of α-ketoglutarate (5 g/L or 15 g/L) to a culture medium resulted in an approximate two days reduction in time to detection (TTD) of growth in *Mycobacterium avium, Mycobacterium intracellulare* and *Mycobacterium tuberculosis* cultures when compared to a culture medium not containing α-ketoglutarate.

Similar experiments were performed using different concentrations of iso-citrate, L-malate, oxaloacetic acid, lactate and L-arginine, however, unlike α-ketoglutarate, these other substrates did not show a reduction in TTD (data not shown).

TABLE 3

TTD of *Mycobacteria* species with and without α-ketoglutarate

| Organism | Substrate | Avg. TTD | Std. Dev. TTD | Min. TTD | Max. TTD | No. of positives | No. tested |
|---|---|---|---|---|---|---|---|
| *M. avium 25291* | No-α-keto glutarate | 15.6 | 0.2 | 15.5 | 15.8 | 3 | 3 |
| | α-keto glutarate-5 g | 13.8 | 1.1 | 12.7 | 14.8 | 3 | 3 |
| | α-keto glutarate-15 g | 13.5 | 1.3 | 12.2 | 14.8 | 3 | 3 |
| *M. intracellulare* | No-α-keto glutarate | 11.6 | 1.3 | 10.7 | 13.0 | 3 | 3 |
| 13950 | A-keto glutarate-5 g | 9.0 | 0.3 | 8.7 | 9.2 | 3 | 3 |
| | A-keto glutarate-15 g | 8.8 | 0.4 | 8.5 | 9.2 | 3 | 3 |
| MTB 27294 | No-α-keto glutarate | 15.7 | 0.8 | 14.8 | 16.2 | 3 | 3 |
| | A-keto glutarate-5 g | 14.3 | 0.8 | 13.8 | 15.2 | 3 | 3 |
| | A-keto glutarate-15 g | 13.9 | 0.2 | 13.7 | 14.0 | 3 | 3 |

Example 3

TTD of Mycobacteria Species with Conventional MAS

The effectiveness of the conventional MAS against mycobacteria growth was determined by studying the effect of six drugs including polymyxin B (POLY B), amphotericin B (AMP B), nalidixic acid (NA), trimethoprim (TMP), Azlocillin (AZL) and Vancomycin (VAN). These studies were also performed to identify the drugs and their concentrations that had adverse effects on mycobacteria growth.

For growth performance, conventional/old RF was prepared and different concentrations of six antimicrobials were added. The concentrations were selected as 25-50% levels lower than or higher than the concentrations of conventional MAS which are 1000 units/ml polymyxin B (POLY B), 180 μg/ml amphotericin B (AMP B), 400 μg/ml nalidixic acid (NA), 10.5 μg/ml trimethoprim (TMP), 34 μg/ml Azlocillin (AZL) and 5 μg/ml Vancomycin (VAN).

The growth (as TTD of growth) was determined for *Mycobacterium intracellulare, Mycobacterium kansasii, Mycobacterium scrofulaceum*, and *Mycobacterium tuberculosis* using azlocillin in the culture medium. The suppression of gram positives, gram negatives and yeast that could be present in a sputum sample (referred to as contaminating respiratory flora, or CRF) was also studied in parallel with the same formulations (data not shown).

For this evaluation, the conventional or old MP formulation (bioMérieux, Inc.) was used. Before the inoculation of MP culture bottles with mycobacteria or other bacterial/yeast cultures, 0.5 ml of conventional/old RF with different drugs was added to the conventional BacT/ALERT® MP culture bottles (bioMérieux, Inc.). The colony counts were also performed using Middlebrook 7H10 or sheep blood or tryptic soy agar plates to verify the inoculum levels and purity of cultures. The inoculated MP bottles were loaded at 35-37° C. in BacT/ALERT® 3D (bioMérieux, Inc.) non-rocking system for 35 days for mycobacteria cultures and up to 15 days for other cultures. Time To Detection (TTD) data was collected when the bottles were declared positive by the BacT/ALERT instrument. The results are shown in Tables 4-5 and FIGS. 3-4.

Figure 3:
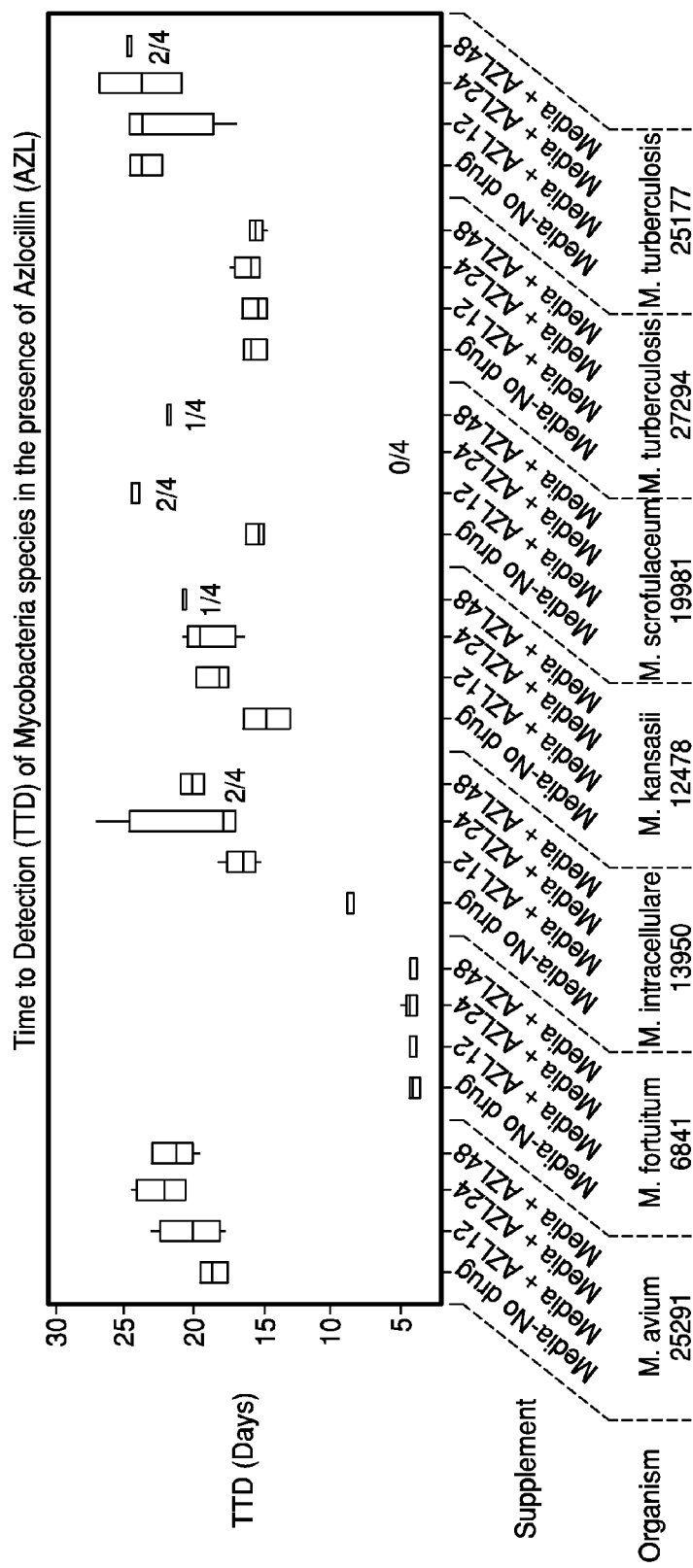
FIG. 3—is a boxplot showing time to detection (TTD) of mycobacteria strains with azlocillin.

As shown in Table 4 and FIG. 3, the use of azlocillin in a culture medium had a negative effect on the growth (as determined by TTD of growth) of *Mycobacterium intracellulare*, *Mycobacterium kansasii*, *Mycobacterium scrofulaceum*, and *Mycobacterium tuberculosis*, when compared to a culture medium that contained no antimicrobial agents.

The growth (as TTD of growth) was determined for *Mycobacterium kansasii*, *Mycobacterium scrofulaceum*, and *Mycobacterium tuberculosis* using vancomycin in the culture medium.

Figure 4:
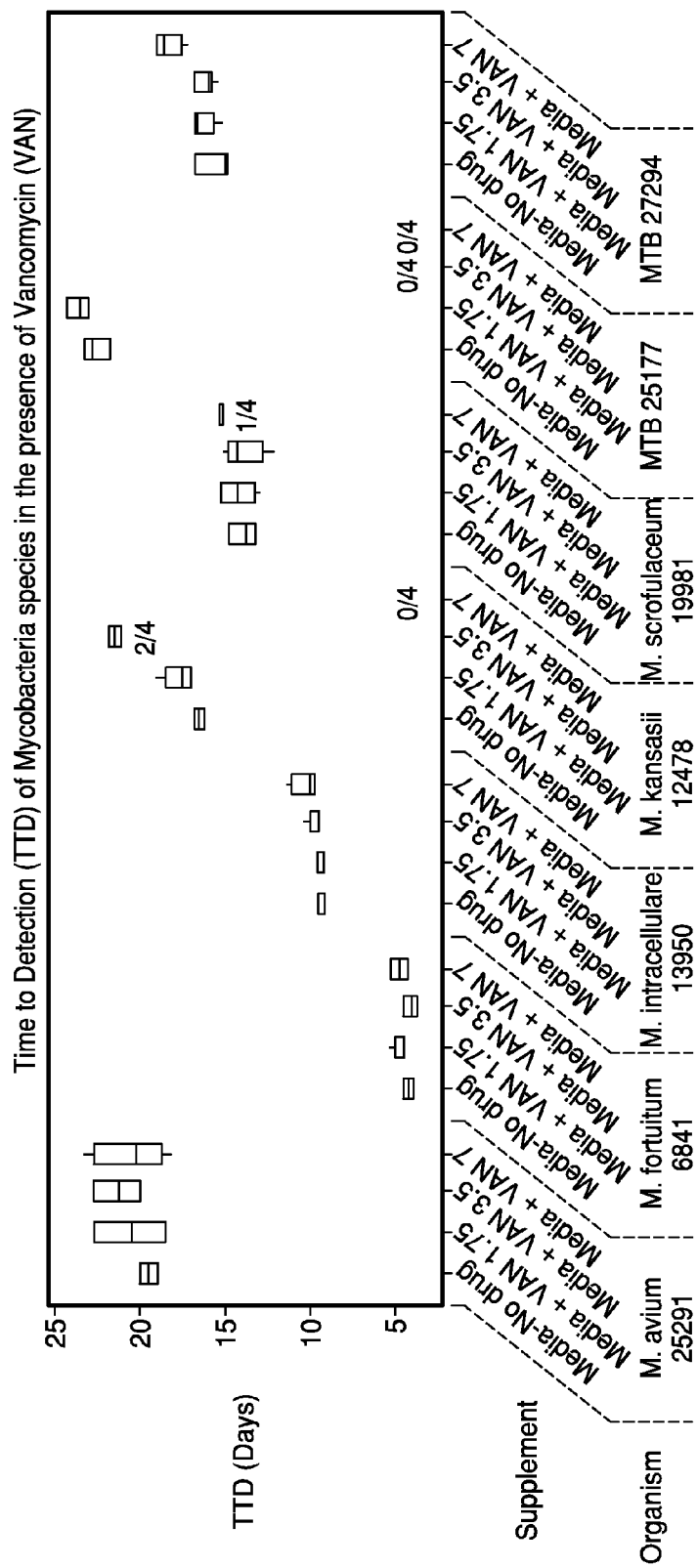
FIG. 4—is a boxplot showing the effect of vancomycin on mycobacterial strain growth.

As shown in Table 5 and FIG. 4, the use of vancomycin in a culture medium had a negative effect on the growth (as determined by TTD of growth) of *Mycobacterium kansasii*, *Mycobacterium scrofulaceum*, and *Mycobacterium tuberculosis*, when compared to a culture medium that contained no antimicrobial agents.

The use of other drugs in a culture medium did not have any adverse impact on mycobacteria growth (data not shown) even at higher concentrations tested. The higher concentrations of drugs were able to suppress most of CRF for 10-15 days with some exceptions of gram negatives (data not shown).

TABLE 4

TTD of *Mycobacteria* species in the presence of Azlocillin (AZL)

| Organism | Supplement | Average TTD | Std. Dev TTD | Min TTD | Max TTD | # Positive | # Tested |
|---|---|---|---|---|---|---|---|
| *M. avium* 25291 | Media + AZL 12 | 20.1 | 2.2 | 17.8 | 22.8 | 4.0 | 4.0 |
| | Media + AZL 24 | 22.2 | 1.8 | 20.7 | 24.3 | 4.0 | 4.0 |
| | Media + AZL 48 | 21.2 | 1.6 | 19.8 | 23.0 | 4.0 | 4.0 |
| | Media − No drug | 18.6 | 0.9 | 17.7 | 19.5 | 3.0 | 3.0 |
| *M. fortuitum* 6841 | Media + AZL 12 | 4.0 | 0.2 | 3.8 | 4.2 | 4.0 | 4.0 |
| | Media + AZL 24 | 4.2 | 0.3 | 3.8 | 4.5 | 4.0 | 4.0 |
| | Media + AZL 48 | 4.1 | 0.2 | 3.8 | 4.3 | 4.0 | 4.0 |
| | Media − No drug | 3.8 | 0.3 | 3.5 | 4.0 | 3.0 | 3.0 |
| *M. intracellulare* 13950 | Media + AZL 12 | 16.4 | 1.1 | 15.3 | 18.0 | 4.0 | 4.0 |
| | Media + AZL 24 | 19.8 | 4.7 | 16.8 | 26.8 | 4.0 | 4.0 |
| | Media + AZL 48 | 20.0 | 1.1 | 19.2 | 20.8 | 2.0 | 4.0 |
| | Media − No drug | 8.5 | 0.2 | 8.3 | 8.7 | 3.0 | 3.0 |
| *M. kansasii* 12478 | Media + AZL 12 | 18.5 | 1.1 | 17.7 | 19.7 | 3.0 | 4.0 |
| | Media + AZL 24 | 18.9 | 1.8 | 16.5 | 20.5 | 4.0 | 4.0 |
| | Media + AZL 48 | 20.5 | #DIV/0! | 20.5 | 20.5 | 1.0 | 4.0 |
| | Media − No drug | 14.8 | 1.8 | 13.0 | 16.5 | 3.0 | 3.0 |
| *M. scrofulaceum* 19981 | Media + AZL 12 | 24.2 | 0.2 | 24.0 | 24.3 | 2.0 | 4.0 |
| | Media + AZL 24 | | | | | | 4.0 |
| | Media + AZL 48 | 21.7 | #DIV/0! | 21.7 | 21.7 | 1.0 | 3.0 |
| | Media − No drug | 15.4 | 0.5 | 15.0 | 16.0 | 3.0 | 3.0 |
| *M. tuberculosis* 27294 | Media + AZL 12 | 15.4 | 0.8 | 14.7 | 16.5 | 4.0 | 4.0 |
| | Media + AZL 24 | 16.0 | 0.9 | 15.3 | 17.3 | 4.0 | 4.0 |
| | Media + AZL 48 | 15.4 | 0.5 | 14.7 | 15.8 | 4.0 | 4.0 |
| | Media − No drug | 15.5 | 0.8 | 14.7 | 16.2 | 3.0 | 3.0 |
| *M. tuberculosis* 25177 | Media + AZL 12 | 22.4 | 3.7 | 17.0 | 24.8 | 4.0 | 4.0 |
| | Media + AZL 24 | 23.8 | 4.2 | 20.8 | 26.8 | 2.0 | 4.0 |
| | Media + AZL 48 | 24.8 | 0.1 | 24.7 | 24.8 | 2.0 | 4.0 |
| | Media − No drug | 23.6 | 1.3 | 22.2 | 24.8 | 3.0 | 3.0 |

TABLE 5

TTD of *Mycobacteria* species in the presence of Vancomycin (VAN)

| Organism | Supplement | Average TTD | Std. Dev TTD | Min TTD | Max TTD | # Positives | # Tested |
|---|---|---|---|---|---|---|---|
| *M. avium* 25291 | Media + VAN 1.75 | 20.6 | 2.2 | 18.5 | 22.8 | 3.0 | 4.0 |
| | Media + VAN 3.5 | 21.2 | 1.6 | 19.8 | 22.7 | 4.0 | 4.0 |
| | Media + VAN 7 | 20.6 | 2.0 | 18.3 | 23.2 | 4.0 | 4.0 |
| | Media − No drug | 19.4 | 0.4 | 19.0 | 19.8 | 3.0 | 3.0 |
| *M. fortuitum* 6841 | Media + VAN 1.75 | 4.7 | 0.3 | 4.5 | 5.2 | 4.0 | 4.0 |
| | Media + VAN 3.5 | 4.1 | 0.3 | 3.7 | 4.5 | 4.0 | 4.0 |
| | Media + VAN 7 | 4.8 | 0.5 | 4.3 | 5.3 | 4.0 | 4.0 |
| | Media − No drug | 4.2 | 0.3 | 4.0 | 4.5 | 3.0 | 3.0 |
| *M. intracellulare* 13950 | Media + VAN 1.75 | 9.4 | 0.1 | 9.2 | 9.5 | 4.0 | 4.0 |
| | Media + VAN 3.5 | 9.7 | 0.3 | 9.5 | 10.2 | 4.0 | 4.0 |
| | Media + VAN 7 | 10.3 | 0.7 | 9.7 | 11.2 | 4.0 | 4.0 |
| | Media − No drug | 9.3 | 0.2 | 9.2 | 9.5 | 3.0 | 3.0 |
| *M. kansasii* 12478 | Media + VAN 1.75 | 17.7 | 0.8 | 17.0 | 18.8 | 4.0 | 4.0 |
| | Media + VAN 3.5 | 21.5 | 0.4 | 21.2 | 21.8 | 2.0 | 4.0 |
| | Media + VAN 7 | | | | | | 4.0 |
| | Media − No drug | 16.5 | 0.2 | 16.3 | 16.7 | 3.0 | 3.0 |

TABLE 5-continued

TTD of *Mycobacteria* species in the presence of Vancomycin (VAN)

| Organism | Supplement | Average TTD | Std. Dev TTD | Min TTD | Max TTD | # Positives | # Tested |
|---|---|---|---|---|---|---|---|
| M. scrofulaceum | Media + VAN 1.75 | 14.2 | 1.0 | 12.8 | 15.3 | 4.0 | 4.0 |
| 19981 | Media + VAN 3.5 | 14.0 | 1.2 | 12.2 | 15.0 | 4.0 | 4.0 |
|  | Media + VAN 7 | 15.3 | — | 15.3 | 15.3 | 1.0 | 1.0 |
|  | Media – No drug | 13.9 | 0.8 | 13.2 | 14.8 | 3.0 | 3.0 |
| MTB 25177 | Media + VAN 1.75 | 23.7 | 0.9 | 23.0 | 24.3 | 2.0 | 4.0 |
|  | Media + VAN 3.5 |  |  |  |  |  | 4.0 |
|  | Media + VAN 7 |  |  |  |  |  | 4.0 |
|  | Media – No drug | 22.6 | 0.8 | 21.8 | 23.3 |  | 3.0 |
| MTB 27294 | Media + VAN 1.75 | 16.3 | 0.7 | 15.3 | 16.8 | 4.0 | 4.0 |
|  | Media + VAN 3.5 | 16.0 | 0.6 | 15.5 | 16.8 | 4.0 | 4.0 |
|  | Media + VAN 7 | 18.3 | 0.9 | 17.2 | 19.0 | 4.0 | 4.0 |
|  | Media – No drug | 15.4 | 1.1 | 14.7 | 16.7 | 3.0 | 3.0 |

Example 4

TTD of Various *Mycobacterium* Species with Various MAS Formulations

To improve TTD of mycobacteria, various drugs were screened for their ability to suppress contaminating respiratory flora (CRF). From these evaluations, fosfomycin was considered to be the best choice for suppression of CRF.

A study was performed to determine the best possible formulation for a new MAS cocktail, various formulations were tested containing different concentrations of TMP, NA, FOS and POLY B. The following formulas were evaluated: (1) NS: New bottle+Nutrient Supplement (NS); (2) RF: Conventional/old MP bottle+Conventional/old Recon Fluid; (3) Formula 1: NS+TMP (30 µg/ml), NA (600 µg/ml), POLY B (1250 units/ml), FOS (600 µg/ml), Amp B (180 µg/ml-PI or IFU); (4) Formula 2: NS+TMP (30 µg/ml), NA (400 ng/ml-PI or IFU), POLY B (1250 units/ml), FOS (600 ng/ml), Amp B (180 ng/ml-PI or IFU); (5) Formula 3: NS+TMP (30 ng/ml), NA (400 ng/ml-PI or IFU), POLY B (1500 units/ml), FOS (600 ng/ml), Amp B (180 ng/ml—PI or IFU); (6) Formula 4: NS+TMP (30 ng/ml), NA (600 ng/ml), POLY B (1250 units/ml), FOS (600 ng/ml), Amp B (180 ng/ml—PI or IFU); and (7) Formula 5: NS+TMP (50 ng/ml), NA (400 ng/ml-PI or IFU), POLY B (1250 units/ml), FOS (600 ng/ml), Amp B (180 ng/ml—PI or IFU); Where TMP is trimethoprim, NA is nalidixic acid, POLY B is polymyxin B, FOS is fosfomycin, and Amp B is amphotericin B.

The new supplement containing fatty acid free (FAF) BSA, 5 long chain fatty acids and of α-ketoglutarate, referred as nutrient supplement (NS), was prepared and filter sterilized as explained previously. The new, autoclavable MP culture bottle (as described hereinabove) was used for this study. Table 6 shows the composition of the new MP culture bottle and nutrient supplement (NS).

TABLE 6

New Culture Bottle and new Nutrient Supplement formulations

| New BacT/ALERT MP culture bottle MP Culture Bottle | |
|---|---|
| Raw Material | g/L |
| Middlebrook | 4.7 |

| Nutrient Supplement (NS) | |
|---|---|
| Material Description | Quantity per liter |
| Glycerol | 50 g |
| Sodium Stearate #1 | 0.113 g |
| Myristic Acid Sodium Salt #2 | 0.167 g |
| Sodium Palmitate #3 | 0.088 g |
| Sodium Oleate #4 | 0.113 g |
| Linoleic Acid Sodium #5 | 0.111 g |
| Bovine Serum Albumin (BSA) | 210 g |
| Catalase | 0.064 g |
| Pancreatic digest of Casein | 20 g |
| Sodium Pyruvate | 20 g |
| Amaranth | 0.04 g |
| AKeto-glutarate | 5 g |

For the new NS, an autoclaved or new BacT/ALERT® MP bottle was used (as described hereinabove) and for conventional/old RF, conventional/old MP bottle (bioMérieux, Inc.) was used. Before the inoculation of old or new MP culture bottles with mycobacteria or other bacterial/yeast cultures, 0.5 ml of nutrient supplement (new NS) or 0.5 ml conventional/old RF with different drugs were added to one set of the BacT/ALERT® MP culture bottles. The conventional MAS (using conventional/old RF) and new MAS formulas (using NS) were added to the second set of MP culture bottles. The experiment was performed with mycobacteria species at 0.5× $10^3$ CFU/ml and CRF cultures at 0.5×$10^5$ CFU/ml. The colony counts were also performed using Middlebrook 7H10 or sheep blood or tryptic soy agar plates to verify the inoculum levels and purity of cultures. The inoculated MP bottles were loaded at 35-37° C. in BacT/ALERT® 3D (bioMérieux, Inc.) non-rocking system for 35 days for mycobacteria cultures and up to 15 days for other cultures. Time To Detection (TTD) data was collected when the bottles were declared positive by the BacT/ALERT® instrument. The results are shown in Table 7 and FIGS. 5A-5F.

All the new MAS formulas achieved better suppression of Gram-negative bacteria as compared to conventional/old MAS. There was breakthrough growth of *Staphylococcus* and *Enterococcus* species with the new formulas as compared to conventional/old MAS.

Figure 5A:
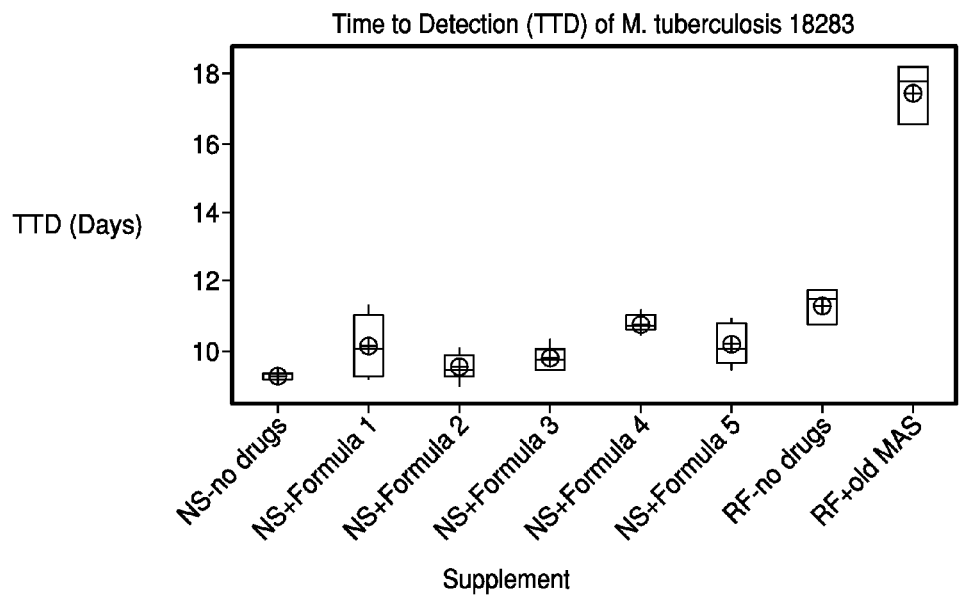
FIG. 5A—is a boxplot showing time to detection (TTD) of *M. tuberculosis* 18283 with various mycobacterial antimicrobial supplement (MAS) formulations.

Table 7 and FIG. 5A show the TTD of *M. tuberculosis* 18283 with various MAS formulations. All 5 new formulations showed an improvement in TTD when compared to the conventional/old formulation for the MAS. The improvement in TTD for *M. tuberculosis* 18283 with the new MAS formulation was approximately 6-8 days.

Figure 5B:
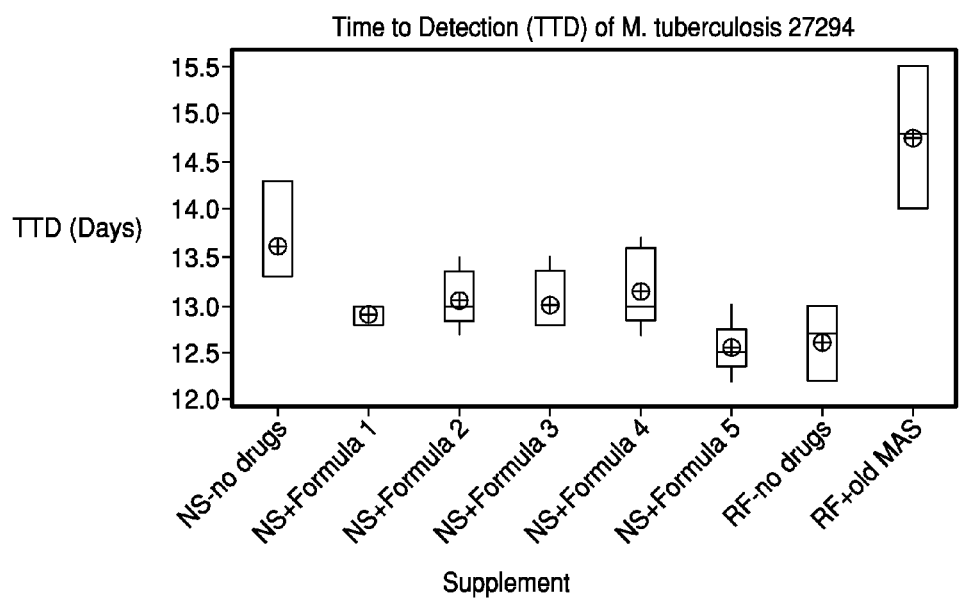
FIG. 5B—is a boxplot showing time to detection (TTD) of *M. tuberculosis* 27294 with various mycobacterial antimicrobial supplement (MAS) formulations.
Figure 5E:
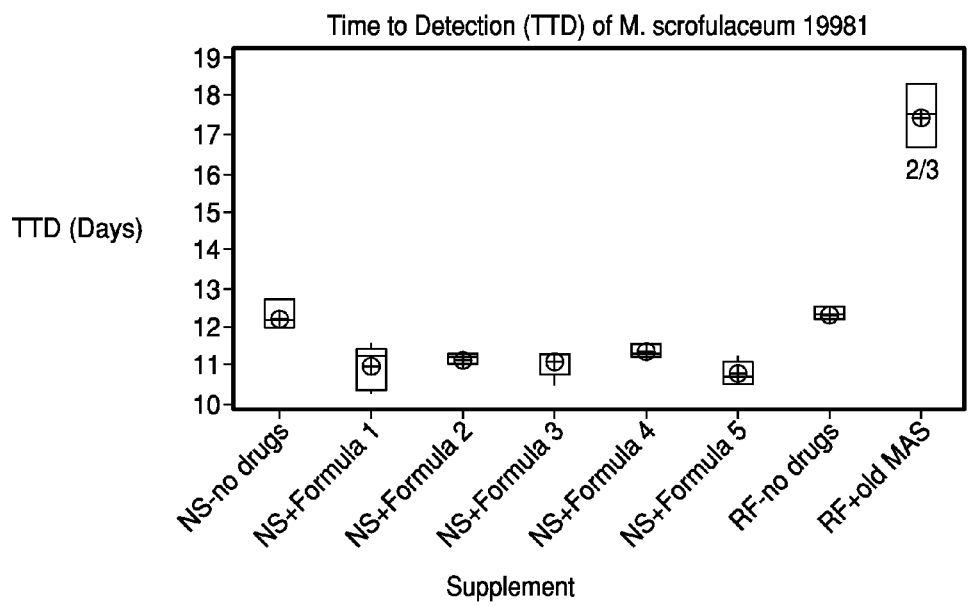
FIG. 5E—is a boxplot showing time to detection (TTD) of *M. scrofulaceum* 19981 with various mycobacterial antimicrobial supplement (MAS) formulations.
Figure 5F:
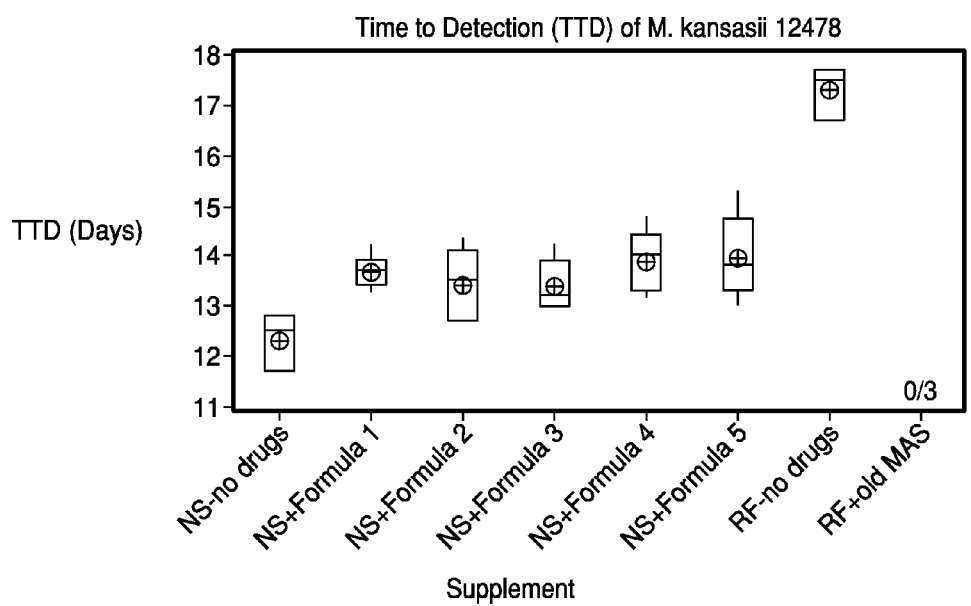
FIG. 5F—is a boxplot showing time to detection (TTD) of *M. kansasii* 12478 with various mycobacterial antimicrobial supplement (MAS) formulations.

Table 7 and FIG. 5B show the TTD of *M. tuberculosis* 27294 with various MAS formulations. All 5 new formulations showed an improvement in TTD when compared to the conventional/old formulation for the MAS. The improvement in TTD for *M. tuberculosis* 27294 with the new MAS formulation was approximately 3-4 days.

Table 7 and FIG. 5C show the TTD of *M. avium* 569 with various MAS formulations. All 5 new formulations showed an improvement in TTD when compared to the conventional/old formulation for the MAS. The improvement in TTD for *M. avium* 569 with the new MAS formulation was approximately 6-7 days.

Table 7 and FIG. 5D show the TTD of *M. intracellulare* 13950 with various MAS formulations. All 5 new formulations showed an improvement in TTD when compared to the conventional/old formulation for the MAS. The improvement in TTD for *M. intracellulare* 13950 with the new MAS formulation was approximately 8-9 days.

Table 7 and FIG. 5E show the TTD of *M. scrofulaceum* 19981 with various MAS formulations. All 5 new formulations showed an improvement in TTD when compared to the conventional/old formulation for the MAS. The improvement in TTD for *M. scrofulaceum* 19981 with the new MAS formulation was approximately 6-7 days. Notably, 2 of the 5 samples tested for *M. scrofulaceum* 19981 showed no growth with the conventional/old MAS formulation.

Table 7 and FIG. 5F show the TTD of *M. kansasii* 12478 with various MAS formulations. All 5 new formulations showed an improvement in TTD when compared to the conventional/old formulation for the MAS. TTD detection for *M. kansasii* 12478 was approximately 13-14 days with the new MAS compared to no growth detected with the conventional/old MAS formulation.

TABLE 7

TTD of various species

| Organism | RF | Supplement | Average TTD | Std. Dev. TTD | Min TTD | Max TTD | # Positive | # Tested |
|---|---|---|---|---|---|---|---|---|
| *M. avium* 569 | 1 | NS − no drugs | 9.2 | 0.5 | 8.7 | 9.7 | 3.0 | 3.0 |
| | 3 | NS + Formula 1 | 9.0 | 0.6 | 8.5 | 10.0 | 5.0 | 5.0 |
| | 4 | NS + Formula 2 | 9.3 | 0.6 | 8.8 | 10.3 | 5.0 | 5.0 |
| | 5 | NS + Formula 3 | 8.4 | 0.3 | 8.0 | 8.7 | 5.0 | 5.0 |
| | 6 | NS + Formula 4 | 8.5 | 0.2 | 8.3 | 8.8 | 5.0 | 5.0 |
| | 7 | NS + Formula 5 | 9.2 | 0.3 | 8.7 | 9.5 | 5.0 | 5.0 |
| | 8 | RF − no drugs | 9.4 | 0.4 | 9.0 | 9.7 | 3.0 | 3.0 |
| | 9 | RF + old MAS | 14.6 | 0.4 | 14.3 | 15.0 | 3.0 | 3.0 |
| *M. intracellulare* 13950 | 1 | NS − no drugs | 9.2 | 0.1 | 9.2 | 9.3 | 3.0 | 3.0 |
| | 3 | NS + Formula 1 | 9.5 | 0.3 | 9.0 | 9.7 | 5.0 | 5.0 |
| | 4 | NS + Formula 2 | 9.4 | 0.1 | 9.3 | 9.5 | 5.0 | 5.0 |
| | 5 | NS + Formula 3 | 9.4 | 0.3 | 9.0 | 9.7 | 5.0 | 5.0 |
| | 6 | NS + Formula 4 | 10.0 | 0.2 | 9.7 | 10.3 | 5.0 | 5.0 |
| | 7 | NS + Formula 5 | 9.2 | 0.2 | 9.0 | 9.5 | 5.0 | 5.0 |
| | 8 | RF − no drugs | 8.1 | 0.1 | 8.0 | 8.2 | 3.0 | 3.0 |
| | 9 | RF + old MAS | 17.2 | 1.3 | 15.8 | 18.2 | 3.0 | 3.0 |
| *M. kansasii* 12478 | 1 | NS − no drugs | 12.3 | 0.6 | 11.7 | 12.8 | 3.0 | 3.0 |
| | 3 | NS + Formula 1 | 13.7 | 0.3 | 13.3 | 14.2 | 5.0 | 5.0 |
| | 4 | NS + Formula 2 | 13.4 | 0.7 | 12.7 | 14.3 | 5.0 | 5.0 |
| | 5 | NS + Formula 3 | 13.4 | 0.5 | 13.0 | 14.2 | 5.0 | 5.0 |
| | 6 | NS + Formula 4 | 13.9 | 0.6 | 13.2 | 14.8 | 5.0 | 5.0 |
| | 7 | NS + Formula 5 | 14.0 | 0.8 | 13.0 | 15.3 | 5.0 | 5.0 |
| | 8 | RF − no drugs | 17.3 | 0.5 | 16.7 | 17.7 | 3.0 | 3.0 |
| | 9 | RF + old MAS | | | | | | 3.0 |
| *M. scrofulaceum* 19981 | 1 | NS − no drugs | 12.3 | 0.4 | 12.0 | 12.7 | 3.0 | 3.0 |
| | 3 | NS + Formula 1 | 11.0 | 0.5 | 10.3 | 11.5 | 5.0 | 5.0 |
| | 4 | NS + Formula 2 | 11.1 | 0.1 | 11.0 | 11.3 | 5.0 | 5.0 |
| | 5 | NS + Formula 3 | 11.1 | 0.3 | 10.5 | 11.3 | 5.0 | 5.0 |
| | 6 | NS + Formula 4 | 11.3 | 0.2 | 11.2 | 11.5 | 5.0 | 5.0 |
| | 7 | NS + Formula 5 | 10.8 | 0.3 | 10.5 | 11.2 | 5.0 | 5.0 |
| | 8 | RF − no drugs | 12.3 | 0.2 | 12.2 | 12.5 | 3.0 | 3.0 |
| | 9 | RF + old MAS | 17.5 | 1.1 | 16.7 | 18.3 | 2.0 | 3.0 |
| MTB 18283 | 1 | NS − no drugs | 9.3 | 0.1 | 9.2 | 9.3 | 3.0 | 3.0 |
| | 3 | NS + Formula 1 | 10.1 | 0.9 | 9.2 | 11.3 | 5.0 | 5.0 |
| | 4 | NS + Formula 2 | 9.5 | 0.4 | 9.0 | 10.0 | 5.0 | 5.0 |
| | 5 | NS + Formula 3 | 9.7 | 0.3 | 9.5 | 10.3 | 5.0 | 5.0 |
| | 6 | NS + Formula 4 | 10.8 | 0.3 | 10.5 | 11.2 | 5.0 | 5.0 |
| | 7 | NS + Formula 5 | 10.1 | 0.6 | 9.5 | 10.8 | 5.0 | 5.0 |
| | 8 | RF − no drugs | 11.3 | 0.5 | 10.8 | 11.7 | 3.0 | 3.0 |
| | 9 | RF + old MAS | 17.5 | 0.9 | 16.5 | 18.2 | 3.0 | 3.0 |

TABLE 7-continued TTD of various species

| Organism | RF | Supplement | Average TTD | Std. Dev. TTD | Min TTD | Max TTD | # Positive | # Tested |
|---|---|---|---|---|---|---|---|---|
| MTB 27294 | 1 | NS – no drugs | 13.6 | 0.6 | 13.3 | 14.3 | 3.0 | 3.0 |
| | 3 | NS + Formula 1 | 12.9 | 0.1 | 12.8 | 13.0 | 5.0 | 5.0 |
| | 4 | NS + Formula 2 | 13.1 | 0.3 | 12.7 | 13.5 | 5.0 | 5.0 |
| | 5 | NS + Formula 3 | 13.0 | 0.3 | 12.8 | 13.5 | 5.0 | 5.0 |
| | 6 | NS + Formula 4 | 13.2 | 0.4 | 12.7 | 13.7 | 5.0 | 5.0 |
| | 7 | NS + Formula 5 | 12.5 | 0.3 | 12.2 | 13.0 | 5.0 | 5.0 |
| | 8 | RF – no drugs | 12.6 | 0.4 | 12.2 | 13.0 | 3.0 | 3.0 |
| | 9 | RF + old MAS | 14.8 | 0.8 | 14.0 | 15.5 | 3.0 | 3.0 |

Example 5

Comparison of Prior MAS Formulation Versus New MAS Formulation for TTD of *M. tuberculosis* Complex Growth The formula of the new MP bottle and nutrient supplement and formula 5 of new MAS were selected for further testing. This study was performed by *M. tuberculosis* complex strains including *Mycobacterium africanum*, *Mycobacterium bovis*, *Mycobacterium microti*, and *Mycobacterium tuberculosis*. The composition of formula 5 was: NS+TMP (50 µg/ml), NA (400 µg/ml-PI or IFU), POLY B (1250 units/ml), FOS (600 µg/ml), Amp B (180 µg/ml—PI or IFU).

For the new MAS formulas and NS, a new, autoclaved BacT/ALERT® MP bottle (as described hereinabove) was used and for conventional/old RF, conventional/old MP bottle (bioMérieux, Inc.) was used. Before the inoculation of old or new MP culture bottles with mycobacteria cultures, 0.5 ml of nutrient supplement (new NS) or 0.5 ml of conventional/old RF with different drugs were added to one set of the BacT/ALERT® MP culture bottles. The conventional MAS (using conventional/old RF) and new MAS formulas (using NS) were added to the second set of MP culture bottles.

The mycobacteria inoculum was $0.5 \times 10^3$ CFU/ml. The colony counts were also performed using Middlebrook 7H10 or sheep blood or tryptic soy agar plates to verify the inoculum levels and purity of cultures. The inoculated MP bottles were loaded at 35-37° C. in BacT/ALERT® 3D (bioMérieux, Inc.) non-rocking system for 35 days for mycobacteria cultures. Time To Detection (TTD) data was collected when the bottles were declared positive by the BacT/ALERT instrument.

The growth (as TTD of growth) was determined for *M. tuberculosis* complex strains comparing the conventional/old RF and MAS (RF+Conventional/old MAS) and the new nutrient supplement and new MAS (NS+New MAS). TTD was determined for four out of five *M. tuberculosis* complex strains i.e. *Mycobacterium africanum*, *Mycobacterium bovis*, *Mycobacterium microti*, and *Mycobacterium tuberculosis* in RF+Conventional/old MAS culture medium and NS+New MAS culture medium. Results are shown in Table 8 and FIG. 6.

As shown in Table 8 and FIG. 6, NS+New MAS shows an approximate 1-10 days improvement in TTD for *M. tuberculosis* complex strain growth when compared to RF+conventional/old MAS.

TABLE 8

TTD of *M. tuberculosis* complex

| Organism | Supplement | Average TTD (days) | Std. Dev. TTD (days) | Min. TTD (days) | Max. TTD (days) | # Positives | # Tested |
|---|---|---|---|---|---|---|---|
| *M. africanum* | NS + Formula 5 | 14.2 | 0.3 | 13.8 | 14.7 | 5.0 | 5.0 |
| 25420 | RF + Old MAS | 15.5 | 0.8 | 14.8 | 16.3 | 3.0 | 3.0 |
| *M. bovis* | NS + Formula 5 | 18.4 | 1.3 | 17.2 | 19.7 | 5.0 | 5.0 |
| 8131 | RF + Old MAS | 20.4 | 2.1 | 18.2 | 22.3 | 3.0 | 3.0 |
| *M. microti* | NS + Formula 5 | 15.0 | 1.4 | 12.8 | 16.3 | 5.0 | 5.0 |
| 19422 | RF + Old MAS | 16.6 | 0.3 | 16.2 | 16.8 | 3.0 | 3.0 |
| MTB 18283 | NS + Formula 5 | 10.1 | 0.2 | 9.7 | 10.2 | 5.0 | 5.0 |
| | RF + Old MAS | 20.9 | 1.8 | 19.2 | 22.7 | 3.0 | 3.0 |
| MTB 25177 | NS + Formula 5 | 19.9 | 1.3 | 18.3 | 21.2 | 5.0 | 5.0 |
| | RF + Old MAS | 32.4 | 1.6 | 31.3 | 34.2 | 3.0 | 3.0 |
| MTB 27294 | NS + Formula 5 | 14.1 | 0.4 | 13.7 | 14.7 | 5.0 | 5.0 |
| | RF + Old MAS | 16.8 | 0.5 | 16.3 | 17.3 | 3.0 | 3.0 |

Example 6

Comparison of Prior MAS Formulation Versus New MAS Formulation for TTD of Mycobacteria Other than Tuberculosis (MOTT) Growth The formula of the new MP bottle, nutrient supplement (NS) and formula 5 of new MAS were selected for further testing. This study was performed by mycobacteria other than tuberculosis (MOTT) strains including *Mycobacterium avium, Mycobacterium intracellulare, Mycobacterium kansasii,* and *Mycobacterium scrofulaceum.* The composition of formula 5 was: NS+TMP (50 µg/ml), NA (400 µg/ml-PI or IFU), POLY B (1250 units/ml), FOS (600 µg/ml), Amp B (180 µg/ml—PI or IFU).

For the new formulas and NS, an autoclaved or new BacT/ALERT® MP bottle (as described hereinabove) was used and for conventional/old RF, conventional/old MP bottle (bioMérieux, Inc.) was used. Before the inoculation of old or new MP culture bottles with mycobacteria cultures, 0.5 ml of nutrient supplement (new NS) or 0.5 ml of conventional/old RF with different drugs were added to one set of the BacT/ALERT® MP culture bottles. The conventional MAS (using conventional/old RF) and new MAS formulas (using NS) were added to the second set of MP culture bottles.

The mycobacteria inoculum was $0.5 \times 10^3$ CFU/ml. The colony counts were also performed using Middlebrook 7H10 or sheep blood or tryptic soy agar plates to verify the inoculum levels and purity of cultures. The inoculated MP bottles were loaded at 35-37° C. in BacT/ALERT 3D (bioMérieux, Inc.) non-rocking system for 35 days for mycobacteria cultures. Time To Detection (TTD) data was collected when the bottles were declared positive by the BacT/ALERT® instrument. Results are shown in Table 9 and FIG. 7.

Figure 7:
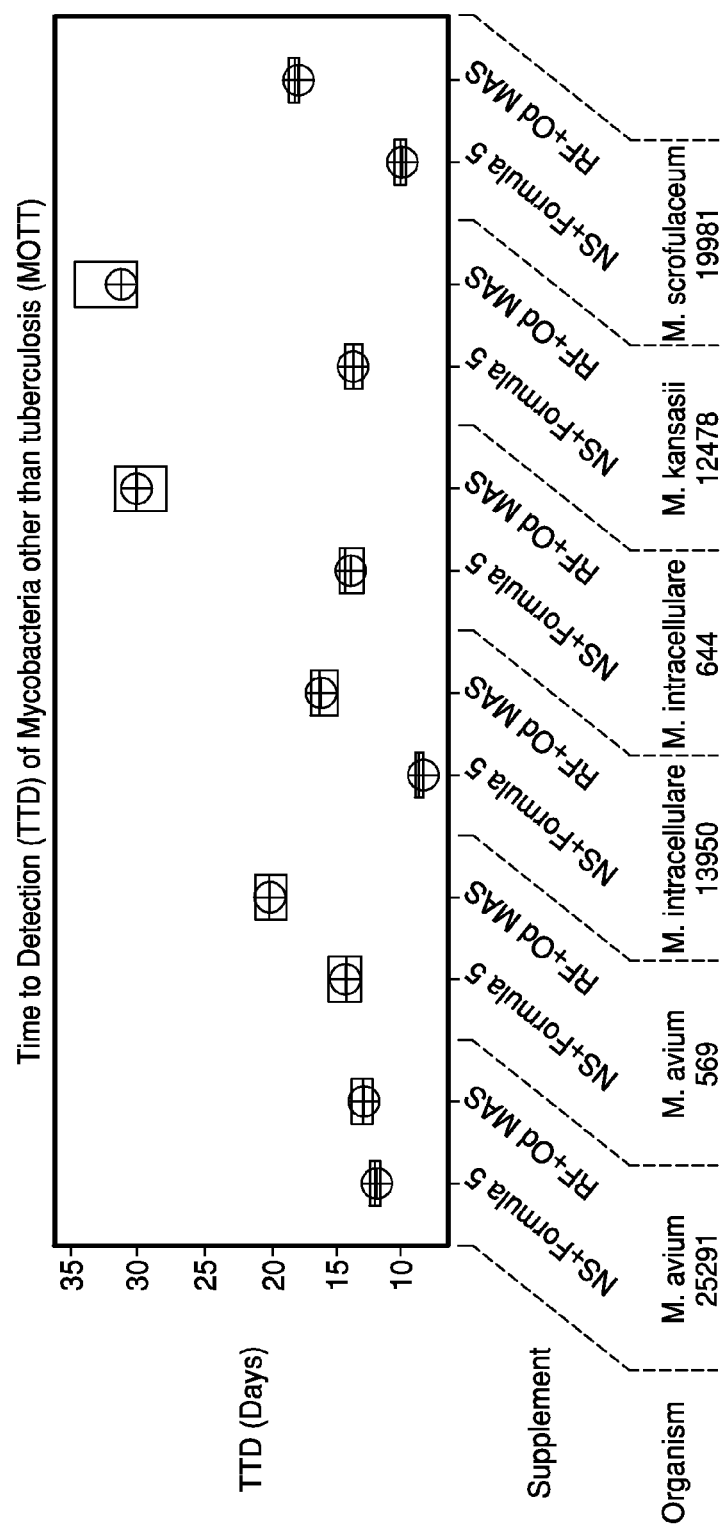
FIG. 7—is a boxplot showing a comparison of the prior MAS formulation versus new mycobacterial antimicrobial supplement (MAS) formulation for time to detection (TTD) of other mycobacteria strain growth.

As shown in Table 9 and FIG. 7, NS+New MAS shows an approximate 1-12 days improvement in TTD for the Mycobacteria other than tuberculosis (MOTT) when compared to RF+Conventional/old MAS.

Example 7

Comparison of Prior MAS Formulation Versus Two New MAS Formulations with Different FOS Concentrations for TTD of *M. tuberculosis* Strains Formula 5 of new MAS was further refined to achieve better suppression of CRF by increasing the FOS concentration from 600 µg/ml to 800 µg/ml. The next study was performed with 10 strains of *M. tuberculosis* at $0.5 \times 10^3$ CFU/ml. Ten *M. tuberculosis* strains comprised of four CDC isolates, five virulent ATCC strains and one QC reference strain.

For the new formulas and new NS, an autoclaved or new BacT/ALERT® MP bottle (as described hereinabove) was used and for conventional/old RF, conventional/old MP bottle (bioMérieux, Inc.) was used. Before the inoculation of old or new MP culture bottles with mycobacteria cultures, 0.5 ml of nutrient supplement (new NS) or 0.5 ml conventional/old RF with different drugs were added to one set of the BacT/ALERT® MP culture bottles. The conventional MAS (using conventional/old RF) and new MAS formulas (using new NS) were added to the second set of MP culture bottles.

The mycobacteria inoculum was $0.5 \times 10^3$ CFU/ml. The colony counts were also performed using Middlebrook 7H10 or sheep blood or tryptic soy agar plates to verify the inoculum levels and purity of cultures. The inoculated MP bottles were loaded at 35-37° C. in BacT/ALERT® 3D (bioMérieux, Inc.) non-rocking system for 35 days for mycobacteria cultures. Time To Detection (TTD) data was collected when the bottles were declared positive by the BacT/ALERT® instrument. Results are shown in Table 10.

As shown in Table 10, the new MAS formulas showed an approximate 2-8 days improvement in TTD for *M. tuberculosis* strains when compared to RF+Conventional/old MAS.

TABLE 9

TTD of *Mycobacteria* other than tuberculosis (MOTT)

| Organism | Supplement | Average TTD (days) | Std. Dev. TTD (days) | Min. TTD (days) | Max. TTD (days) | # Positives | # Tested |
| --- | --- | --- | --- | --- | --- | --- | --- |
| *M. avium* 25291 | NS + Formula 5 | 11.8 | 0.4 | 11.5 | 12.5 | 5.0 | 5.0 |
| | RF + Old MAS | 12.9 | 0.7 | 12.3 | 13.7 | 3.0 | 3.0 |
| *M. avium* 569 | NS + Formula 5 | 14.2 | 1.3 | 12.7 | 15.7 | 5.0 | 5.0 |
| | RF + Old MAS | 20.0 | 1.8 | 18.7 | 21.2 | 2.0 | 3.0 |
| *M. intracellulare* 13950 | NS + Formula 5 | 8.6 | 0.3 | 8.2 | 9.0 | 5.0 | 5.0 |
| | RF + Old MAS | 16.0 | 0.9 | 15.0 | 16.8 | 3.0 | 3.0 |
| *M. intracellulare* 644 | NS + Formula 5 | 13.8 | 1.0 | 12.7 | 14.7 | 5.0 | 5.0 |
| | RF + Old MAS | 29.9 | 2.6 | 28.0 | 31.7 | 2.0 | 3.0 |
| *M. kansasii* 12478 | NS + Formula 5 | 13.6 | 0.6 | 12.8 | 14.5 | 5.0 | 5.0 |
| | RF + Old MAS | 31.5 | 2.6 | 30.0 | 34.5 | 3.0 | 3.0 |
| *M. scrofulaceum* 19981 | NS + Formula 5 | 10.0 | 0.3 | 9.7 | 10.5 | 5.0 | 5.0 |
| | RF + Old MAS | 17.9 | 0.3 | 17.7 | 18.2 | 3.0 | 3.0 |

TABLE 10

TTD of various strains of *M. tuberculosis* with new MAS formulas containing
600 μg/ml (MAS 5) and 800 μg/ml (Formula 5 + FOS 200 μg/ml)

| Organism | Strain ID | Supplement | Average TTD (days) | Std. Dev. TTD (days) | Min. TTD (days) | Max. TTD (days) | # Positive | # Tested |
|---|---|---|---|---|---|---|---|---|
| *Mycobacterium tuberculosis* | 2663 | NS + Formula 5 | 15.1 | 0.8 | 14.0 | 16.0 | 5.0 | 5.0 |
| | | NS + Formula 5 + FOS 200 | 15.3 | 0.3 | 14.8 | 15.7 | 5.0 | 5.0 |
| | | RF + Old MAS | 17.9 | 0.2 | 17.7 | 18.3 | 5.0 | 5.0 |
| | 2677 | NS + Formula 5 | 17.3 | 0.5 | 16.7 | 18.0 | 5.0 | 5.0 |
| | | NS + Formula 5 + FOS 200 | 17.2 | 0.6 | 16.5 | 18.0 | 5.0 | 5.0 |
| | | RF + Old MAS | 22.1 | 0.6 | 21.3 | 22.8 | 5.0 | 5.0 |
| | 18283 | NS + Formula 5 | 8.9 | 0.5 | 8.3 | 9.5 | 5.0 | 5.0 |
| | | NS + Formula 5 + FOS 200 | 9.5 | 0.3 | 9.0 | 9.7 | 5.0 | 5.0 |
| | | RF + Old MAS | 17.0 | 0.8 | 16.0 | 18.2 | 5.0 | 5.0 |
| | 18292 | NS + Formula 5 | 13.9 | 0.7 | 13.3 | 14.7 | 5.0 | 5.0 |
| | | NS + Formula 5 + FOS 200 | 14.1 | 0.3 | 13.7 | 14.5 | 5.0 | 5.0 |
| | | RF + Old MAS | 15.8 | 0.8 | 15.2 | 17.2 | 5.0 | 5.0 |
| | 25177 | NS + Formula 5 | 16.0 | 0.4 | 15.5 | 16.3 | 5.0 | 5.0 |
| | | NS + Formula 5 + FOS 200 | 16.3 | 0.8 | 15.2 | 17.3 | 5.0 | 5.0 |
| | | RF + Old MAS | 19.1 | 0.3 | 18.8 | 19.5 | 5.0 | 5.0 |
| | 27294 | NS + Formula 5 | 14.1 | 0.4 | 13.5 | 14.5 | 5.0 | 5.0 |
| | | NS + Formula 5 + FOS 200 | 14.5 | 0.5 | 13.8 | 15.2 | 5.0 | 5.0 |
| | | RF + Old MAS | 16.3 | 0.4 | 15.7 | 16.7 | 5.0 | 5.0 |
| | 35822 | NS + Formula 5 | 15.0 | 0.8 | 13.7 | 16.0 | 5.0 | 5.0 |
| | | NS + Formula 5 + FOS 200 | 15.7 | 0.3 | 15.3 | 16.2 | 5.0 | 5.0 |
| | | RF + Old MAS | 17.9 | 0.6 | 17.2 | 18.8 | 5.0 | 5.0 |
| | 35837 | NS + Formula 5 | 14.8 | 1.0 | 13.5 | 16.3 | 5.0 | 5.0 |
| | | NS + Formula 5 + FOS 200 | 15.2 | 0.2 | 15.0 | 15.3 | 5.0 | 5.0 |
| | | RF + Old MAS | 17.8 | 0.4 | 17.2 | 18.2 | 5.0 | 5.0 |
| | 35838 | NS + Formula 5 | 15.5 | 0.6 | 14.8 | 16.2 | 5.0 | 5.0 |
| | | NS + Formula 5 + FOS 200 | 15.7 | 0.4 | 15.2 | 16.2 | 5.0 | 5.0 |
| | | RF + Old MAS | 17.0 | 0.6 | 16.2 | 17.5 | 5.0 | 5.0 |

Example 8

Comparison of Prior MAS Formulation Versus Two New MAS Formulations with Different FOS Concentrations for Suppression of Contaminating Respiratory Flora (CRF)

Formula 5 of new MAS was further refined to achieve better suppression of CRF by increasing the FOS concentration from 600 ng/ml to 800 ng/ml. Growth or no growth (NG) was determined for various gram positive or gram negative bacterial and yeast cultures by comparing the conventional/old RF and MAS (RF+Conventional/old MAS) and new nutrient supplement and new MAS formulations NS+new MAS). The new MAS formulations contained formula 5+200 ng/ml FOS (a total of 800 ng/ml FOS). CRF were tested were tested at $0.6 \times 10^4$ CFU/ml. The colony counts were also performed using sheep blood or tryptic soy agar plates to verify the inoculum levels and purity of cultures. The inoculated MP bottles were loaded at 35-37° C. in BacT/ALERT® 3D (bioMérieux, Inc.) non-rocking system for 15 days for all cultures. Time To Detection (TTD) data was collected when the bottles were declared positive by the BacT/ALERT® instrument.

Table 11 shows that the new formulation of MAS was a better formulation to suppress the growth of CRF when compared to conventional/old MAS formulation.

TABLE 11

Table showing suppression of contaminating respiratory flora (CRF)

| Organism | Strain ID | Supplement | Breakthrough Contamination |
|---|---|---|---|
| *Candida albicans* | 11006 | NS + Formula 5 | NG |
| | | NS + Formula 5 + FOS 200 | NG |
| | | RF + Old MAS | NG |
| | 302876 | NS + Formula 5 | NG |
| | | NS + Formula 5 + FOS 200 | NG |
| | | RF + Old MAS | 1/5 |
| *Enterococcus faecalis* | 8711 | NS + Formula 5 | 5/5 |
| | | NS + Formula 5 + FOS 200 | 1/5 |
| | | RF + Old MAS | NG |
| | 8340 (VRE) | NS + Formula 5 | 5/5 |
| | | NS + Formula 5 + FOS 200 | NG |
| | | RF + Old MAS | 3/5 |
| *Klebsiella pneumoniae* | 109241 | NS + Formula 5 | NG |
| | | NS + Formula 5 + FOS 200 | NG |
| | | RF + Old MAS | NG |
| *Pseudomonas aeruginosa* | 27853 | NS + Formula 5 | NG |
| | | NS + Formula 5 + FOS 200 | NG |
| | | RF + Old MAS | 1/5 |

TABLE 11-continued

Table showing suppression of contaminating respiratory flora (CRF)

| Organism | Strain ID | Supplement | Breakthrough Contamination |
|---|---|---|---|
| | 106159 | NS + Formula 5 | NG |
| | | NS + Formula 5 + FOS 200 | NG |
| | | RF + Old MAS | NG |
| Staphylococcus aureus | 12535 | NS + Formula 5 | 5/5 |
| | | NS + Formula 5 + FOS 200 | NG |
| | | RF + Old MAS | NG |
| | 25923 | NS + Formula 5 | 5/5 |
| | | NS + Formula 5 + FOS 200 | 2/5 |
| | | RF + Old MAS | NG |
| | 13305 (MRSA) | NS + Formula 5 | 5/5 |
| | | NS + Formula 5 + FOS 200 | NG |
| | | RF + Old MAS | NG |
| Staphylococcus epidermidis | 7104 | NS + Formula 5 | 5/5 |
| | | NS + Formula 5 + FOS 200 | 1/5 |
| | | RF + Old MAS | NG |
| Stenotrophomonas maltophilia | 13637 | NS + Formula 5 | NG |
| | | NS + Formula 5 + FOS 200 | NG |
| | | RF + Old MAS | NG |
| | 106259 | NS + Formula 5 | 5/5 |
| | | NS + Formula 5 + FOS 200 | NG |
| | | RF + Old MAS | 2/5 |
| Streptococcus oralis | 12975 | NS + Formula 5 | NG |
| | | NS + Formula 5 + FOS 200 | NG |
| | | RF + Old MAS | NG |
| Streptococcus pneumoniae | 6305 | NS + Formula 5 | 5/5 |
| | | NS + Formula 5 + FOS 200 | NG |
| | | RF + Old MAS | NG |

That which is claimed is:

1. A kit for enhanced growth and detecting of mycobacteria in a culture medium, said kit comprising: (1) a culture bottle containing a base culture medium; (2) a nutrient supplement comprising fatty acid free BSA, one or more long chain fatty acids, and α-ketoglutarate, an α-ketoglutarate precursor or an α-ketoglutarate derivative selected from the group consisting of glutamate, isocitrate, oxalosuccinate, or mixtures thereof; and (3) an antimicrobial supplement comprises one or more antimicrobial agents for suppressing the growth of contaminating respiratory flora in said culture medium; each separately housed therein; wherein said nutrient supplement and said antimicrobial supplement are added to said culture bottle, and wherein said kit allows for enhanced growth of mycobacteria compared to a kit not containing a supplement comprising fatty acid-free BSA and one or more long chain fatty acids.

2. The kit of claim 1, wherein said enhanced growth comprises reducing the time to detection of mycobacteria growth by at least about 1 days.

3. The kit of claim 1, wherein said base culture medium is Middlebrook 7H9.

4. The kit of claim 1, wherein said base culture medium does not contain heat liable components.

5. The kit of claim 4, wherein said culture bottle and said base culture medium are sterilized by autoclaving.

6. The kit of claim 1, wherein said one or more long chain fatty acids are fatty acids having 10 or more carbon atoms.

7. The kit of claim 6, wherein said fatty acids are selected from the group consisting of capric acid, myristic acid, palmitic acid, stearic acid, oleic acid, linoleic acid, and salts thereof.

8. The kit of claim 1, wherein said antimicrobial supplement comprises fosfomycin.

9. The kit of claim 8, wherein said antimicrobial supplement further comprises one or more additional antibiotics selected from the group consisting of polymyxin B, vancomycin, azlocillin, amphotericin B, nalidixic acid, and trimethoprim.

10. The kit of claim 9, wherein said antimicrobial supplement further comprises polymyxin B, vancomycin, amphotericin B, nalidixic acid, and trimethoprim.

* * * * *